(12) United States Patent
Frank

(10) Patent No.: US 8,445,517 B2
(45) Date of Patent: May 21, 2013

(54) STAT MODULATORS

(75) Inventor: David A. Frank, Lexington, MA (US)

(73) Assignee: Dana-Farber Cancer Institute, Boston, MA (US)

( * ) Notice: Subject to any disclaimer, the term of this patent is extended or adjusted under 35 U.S.C. 154(b) by 406 days.

(21) Appl. No.: 12/653,342

(22) Filed: Dec. 11, 2009

(65) Prior Publication Data

US 2011/0144043 A1  Jun. 16, 2011

(51) Int. Cl.
*A61K 31/44* (2006.01)

(52) U.S. Cl.
USPC ......................................... 514/336; 514/256

(58) Field of Classification Search
USPC ................................ 514/256, 336
See application file for complete search history.

(56) References Cited

U.S. PATENT DOCUMENTS

| | | |
|---|---|---|
| 2003/0157711 A1 | 8/2003 | Oh |
| 2004/0010001 A1 | 1/2004 | Au et al. |
| 2004/0063769 A1 | 4/2004 | Borisy et al. |
| 2004/0147561 A1 | 7/2004 | Zhong et al. |
| 2007/0031871 A1 | 2/2007 | Jove et al. |

OTHER PUBLICATIONS

Li et al. CAS: 150: 345478, 2009.*
Nelson et al. CAS: 150: 28568, 2008.*
Darnell, J, Science 1997; 227: 1630-1635.
Ihle, J. Cell 1996; 84:331-334.
Alvarez, JV, et al. Cancer Res. 2005; 65(12): 5054-62.
Frank, DA Cancer Tret. Res. 2003; 115:267-291.
Bowman T. et al. Oncogene 2000; 19(21): 2474-88.
Song et al. PNAS; 20(13); 4700-4705(2005).
Hilfiker-Kleiner at al., Cir. Res. 95: 187-195(2004).
Stephanou, J. Cell. Mol. Med., 8(4): 519-525 (2004).

* cited by examiner

*Primary Examiner* — Rei-tsang Shiao
(74) *Attorney, Agent, or Firm* — Edwards Wildman Palmer LLP; Peter F. Corless; Richard B. Emmons

(57) ABSTRACT

The present invention is directed to methods, kits and compositions for modulating the activity of Stat molecules (e.g., Stat1, Stat3 and Stat5). The compounds of the invention are useful for treating and/or preventing disorders characterized by Stat dysregulation, such as hyperproliferative disorders. Further, the compounds of the present invention are also useful in culturing stem cells and treating ischemic disorders.

8 Claims, 5 Drawing Sheets

Proliferation of U266 human myeloma cells treated with pimozide

2-NP

STAT MODULATORS

RELATED APPLICATION(S)

This application is a continuation of PCT/US2008/007349 filed Jun. 12, 2008 which claims the benefit of U.S. Provisional Application No. 60/934,535, filed on Jun. 14, 2007. The entire teachings of the above application(s) are incorporated herein by reference.

BACKGROUND

Cancer is characterized by the inappropriate growth or survival of a malignant cell compared to its normal counterpart. Under physiologic conditions, the survival, proliferation, and differentiation of cells is controlled by growth factors, cytokines, and hormones. It is not surprising that the intracellular pathways activated by these factors, which promote the physiologic growth and survival of cells, can be subverted in cancer as a result of the underlying mutations in a tumor cell.

Although cytokines and hormones can trigger the activation of a number of intracellular signaling pathways, it is becoming increasingly clear that members of the Stat family of transcription factors are key mediators of their effects (Darnell J E, Jr. Science 1997; 277:1630-1635; Ihle J N. Cell 1996; 84:331-334). For example, Stats have been found to function inappropriately in many human malignancies (Alvarez J V, Febbo P G, Ramaswamy S, Loda M, Richardson A, Frank D A. Cancer Res 2005; 65(12):5054-62; Frank D A. Cancer Treat. Res. 2003; 115:267-291; Bowman T, et al. Oncogene 2000; 19(21):2474-88). Further, compounds which inhibit Stat3 activity inhibit the proliferation of breast cancer cells (Song et al., PNAS; 20(13); 4700-4705 (2005)).

However, compounds which activate Stat3 may also have beneficial effects. For example, activated Stat3 was shown to protect tissue from ischemic injury and heart failure (Hilfiker-Kleiner et al., Cir. Res. 95:187-195 (2004); Stephanou, J. Cell. Mol. Med., 8(4):519-525 (2004)). Furthermore, Stat3 activation increases self-renewal and in-vitro proliferation of stem cells (U.S. Publication No. 2003/0157711, filed Feb. 18, 2003).

SUMMARY OF THE INVENTION

The present invention is directed to methods, kits and compositions for modulating the activity of Stat molecules (e.g., Stat1, Stat3 and Stat5). The compounds of the invention are useful for treating and/or preventing disorders characterized by Stat dysregulation, such as hyperproliferative disorders. Further, the compounds of the present invention are also useful in culturing stem cells and treating ischemic disorders.

In a first aspect, the present invention is directed to a method for treating or preventing a hyperproliferative disorder in an individual. The method involves administering to an individual in need thereof a pharmacologically effective dose of pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-benzodioxol-5-yl)-1,6-dimethyl-pyrimido[5,4-e]-1,2,4-triazine-5,7(1H,6H)-dione, 2-(1,8-Naphthyridin-2-yl)phenol or 3-(2-hydroxyphenyl)-3-phenyl-N,N-dipropylpropanamide or a salt or ester thereof.

In another aspect, the invention is directed to a method of treating a hyperproliferative disorder in an individual. The method includes identifying a subject as in need of inhibition of Stat3 activity and administering a pharmacologically effective dose of pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-benzodioxol-5-yl)-1,6-dimethyl-pyrimido[5,4-e]-1,2,4-triazine-5,7(1H, 6H)-dione or 3-(2-hydroxyphenyl)-3-phenyl-N,N-dipropylpropanamide or a salt or ester thereof.

In another aspect, the invention is directed to a method for inhibiting Stat3 activity in a cell. The method involves contacting the cell with an effective dose of pyrimethamine, pimozide, guanabenz acetate, alprenolol hydrochloride, nifuroxazide, solanine alpha, fluoxetine hydrochloride, ifosfamide, pyrvinium pamoate and moricizine hydrochloride, 3-(1,3-benzodioxol-5-yl)-1,6-dimethyl-pyrimido[5,4-e]-1,2, 4-triazine-5,7(1H,6H)-dione or 3-(2-hydroxyphenyl)-3-phenyl-N,N-dipropylpropanamide or a salt or ester thereof and detecting a Stat3 activity in the cell.

In yet another aspect, the invention is directed to a method for inducing Stat3 activity in a cell. The method involves contacting the cell with an effective dose of mebendazole, nocodazole, nortriptyline hydrochloride, zimelidine dihydrochloride monohydrate, adenosine 5'-monophosphate monohydrate, promazine hydrochloride, podophyllotoxin, ribavirin, deptropine citrate, or 4-(3,4-Dimethyl-phenoxy)-N-hydroxy-benzamidine or a salt or ester thereof and detecting Stat3 activity in the cell.

In another aspect, the present invention is directed to a method for treating or preventing a hyperproliferative disorder in an individual. The method involves administering to an individual in need thereof a pharmacologically effective dose of a compound of Formula I:

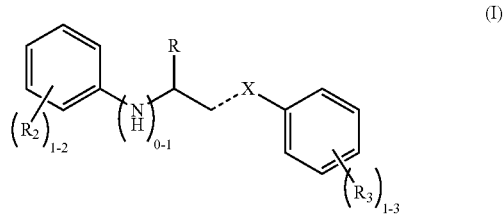

wherein

---- represents a single bond, a double bond, or a triple bond;

X is selected from the group consisting of —O—, —C—, —CH—, —CH$_2$—, and CR$_1$ where R$_1$ is 3-benzenesulfinic acid;

R is =O or H;

each R$_2$ is independently selected from the group consisting of H, —Cl, —NO$_2$, and —C(O)OCH$_3$, or two R$_2$ substituents are connected by —OCH$_2$CH$_2$O— to form a bicyclic ring; and each R$_3$ is independently selected from the group consisting of H, —Cl, —CH$_2$CH$_3$, —OH, —OCH$_3$, and —NO$_2$, and salts, esters or silanyl coordinated species thereof.

In yet another aspect, the present invention is directed to a method for treating or preventing a hyperproliferative disorder in an individual. The method involves administering to an individual in need thereof a pharmacologically effective dose of a compound of Formula II:

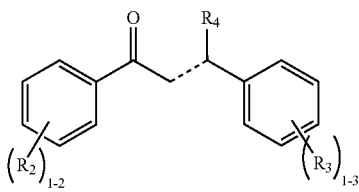

wherein
___ represents a double bond or a triple bond;
$R_4$ is H, 3-benzenesulfinic acid, or absent when ___ represents a triple bond;
R is =O or H;
each $R_2$ is H or two $R_2$ substituents are connected by —OCH$_2$CH$_2$O— to form a bicyclic ring; and
each $R_3$ is independently selected from the group consisting of H, —CH$_2$CH$_3$, —OH, —OCH$_3$, and —NO$_2$ and salts, esters or silanyl coordinated species thereof.

In still another aspect, the present invention is directed to a method for treating or preventing a hyperproliferative disorder in an individual. The method involves administering to an individual in need thereof a pharmacologically effective dose of a compound of Formula III:

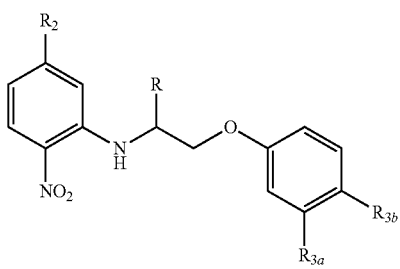

wherein
R is =O or H;
$R_2$ is H or —Cl;
$R_{3a}$ is H or —OCH$_3$; and
$R_{3b}$ is H or Cl. and —NO$_2$ and salts, esters or silanyl coordinated species thereof.

In yet another aspect, the invention is directed to a method for treating or preventing a hyperproliferative disorder in an individual, comprising administering to an individual in need thereof a pharmacologically effective dose a compound of Formula IV:

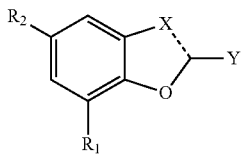

wherein
___ represents a single or a double bond;
$R_1$ is H or —OCH$_3$;
$R_2$ is selected from the group consisting of H, —OCH$_3$, —(CH$_2$)$_2$C(O)NH(CH$_2$)$_2$OH and —NO$_2$;
X is —CR$_3$ or NR$_3$, and R$_3$ is H or —C(O)OCH$_2$CH$_3$; and Y is 5-nitro-thiophen-2-yl or a phenyl, optionally substituted with one or more substituents selected from phenoxy or methoxy and salts, esters or silanyl coordinated species thereof.

In still another aspect, the present invention is directed to a method for treating or preventing a hyperproliferative disorder in an individual. The method involves administering to an individual in need thereof a pharmacologically effective dose of a compound selected from the group consisting of

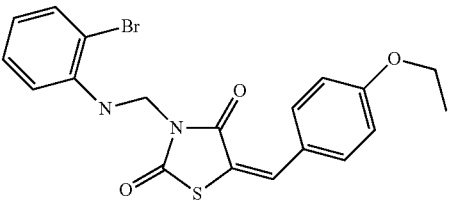

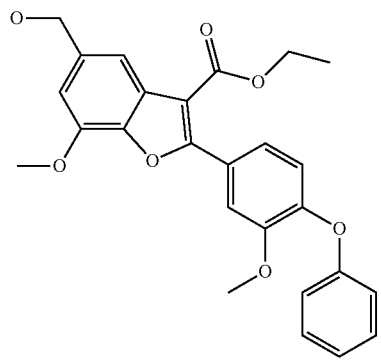

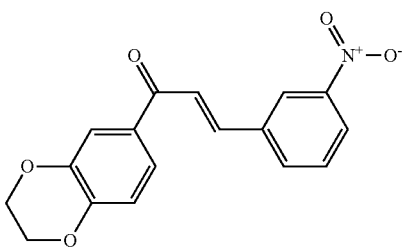

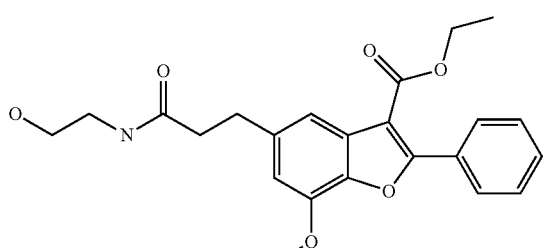

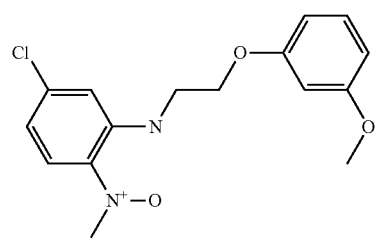

-continued

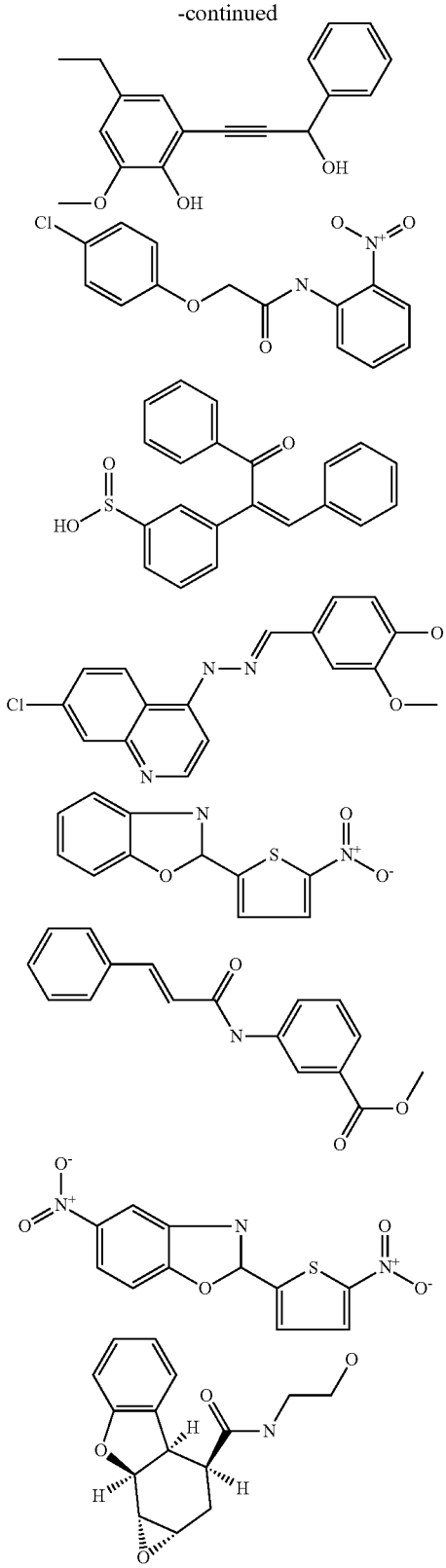

and salts or esters thereof.

In yet another aspect, the invention is directed to a method of inducing Stat 1 activity by contacting a cell with an effective dose of the compound of Formula I, II, III, IV or Table 1.

In another aspect, the invention is directed to treating or preventing an ischemic injury in an individual. The method includes administering, to an individual in need thereof, a pharmacologically effective dose of mebendazole, nocodazole, nortriptyline hydrochloride, zimelidine dihydrochloride monohydrate, adenosine 5'-monophosphate monohydrate, promazine hydrochloride, podophyllotoxin, ribavirin, deptropine citrate, or 4-(3,4-Dimethyl-phenoxy)-N-hydroxybenzamidine or a salt or ester thereof.

In still another aspect of the invention, the invention is directed to a method for maintaining a stem cell in an undifferentiated state. The method includes contacting the stem cell with a pharmacologically effective dose of mebendazole, nocodazole, nortriptyline hydrochloride, zimelidine dihydrochloride monohydrate, adenosine 5'-monophosphate monohydrate, promazine hydrochloride, podophyllotoxin, ribavirin, or 4-(3,4-Dimethyl-phenoxy)-N-hydroxy-benzamidine or a salt or ester thereof.

The invention is also directed to cells for screening Stat-3 modulators (cell lines deposited under ATCC Nos., deposited on), Stat-1 modulators (cell lines deposited under ATCC Nos. [ ], deposited on) and Stat-5 modulators (cell lines deposited under ATCC Nos. [ ], deposited on).

In still another aspect, the invention is directed to a method for screening for a Stat-3 activator. The method includes incubating a cell (ATCC Nos. [ ]) in the presence and absence of a candidate modulator, and detecting a signal from the reporter molecule. The cell has a Stat3 regulatory element operatively linked to a reporter molecule. An increase in the signal in the presence of the candidate modulator when compared with the signal in the absence of said candidate modulator is indicative of a Stat-3 activator.

In yet another aspect, the invention is directed to a method for screening for a Stat-3 inhibitor. The method involves incubating a cell in the presence and absence of a candidate modulator and detecting a signal from the reporter molecule. The cell has a Stat3 regulatory element operatively linked to a reporter molecule. A decrease in the signal in the presence of the candidate modulator when compared with the signal in the absence of the candidate modulator is indicative of a Stat-3 inhibitor.

In still another aspect, the invention is directed to a method for screening for a Stat-1 activator. The method includes incubating a cell (ATCC Nos. [ ]) in the presence and absence of a candidate modulator, and detecting a signal from the reporter molecule. The cell has a Stat1 regulatory element operatively linked to a reporter molecule. An increase in the signal in the presence of the candidate modulator when compared with the signal in the absence of said candidate modulator is indicative of a Stat-1 activator.

In yet another aspect, the invention is directed to a method for screening for a Stat-1 inhibitor. The method involves incubating a cell in the presence and absence of a candidate modulator and detecting a signal from the reporter molecule. The cell has a Stat1 regulatory element operatively linked to a reporter molecule. A decrease in the signal in the presence of the candidate modulator when compared with the signal in the absence of the candidate modulator is indicative of a Stat-1 inhibitor.

In still another aspect, the invention is directed to a method for screening for a Stat-5 activator. The method includes incubating a cell (ATCC Nos. [ ]) in the presence and absence of a candidate modulator, and detecting a signal from the reporter molecule. The cell has a Stat1 regulatory element operatively linked to a reporter molecule. An increase in the signal in the presence of the candidate modulator when compared with the signal in the absence of said candidate modulator is indicative of a Stat-5 activator.

In yet another aspect, the invention is directed to a method for screening for a Stat-5 inhibitor. The method involves incubating a cell in the presence and absence of a candidate modulator and detecting a signal from a reporter molecule. The cell has a Stat5 regulatory element operatively linked to a reporter molecule. A decrease in the signal in the presence of the candidate modulator when compared with the signal in the absence of the candidate modulator is indicative of a Stat-5 inhibitor.

In a further aspect, the invention is directed to kits and compositions for practicing any of the methods of the invention.

DETAILED DESCRIPTION

Figure 1:
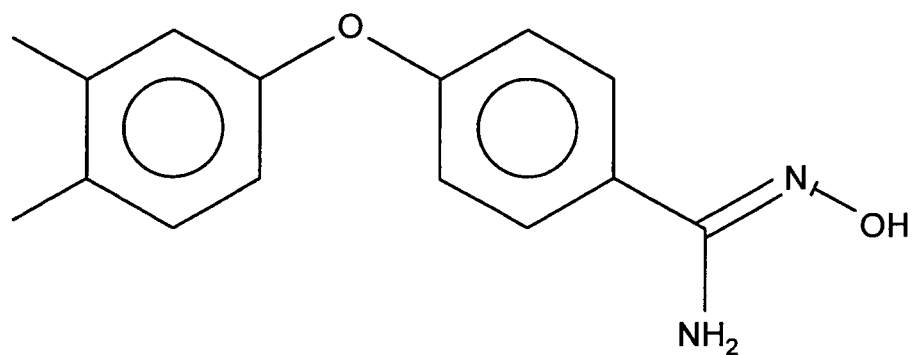
FIG. 1 illustrate the structure of the Stat3 activator 4-(3,4-dimethylphenoxy)-N-hydroxy-benzenecarboximidamide, also known as 4-(3,4-Dimethyl-phenoxy)-N-hydroxy-benzamidine.
Figure 2:
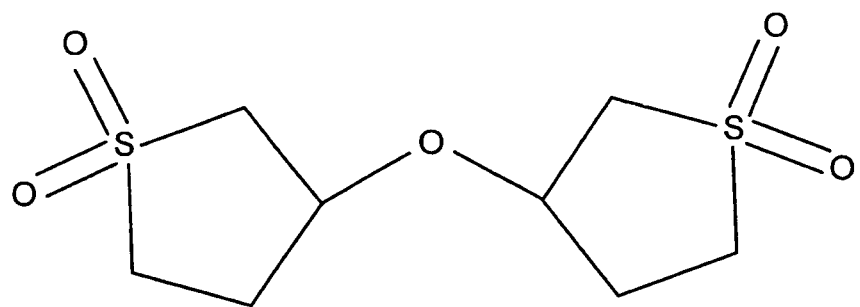
FIG. 2 illustrates the chemical structure of the Stat3 inhibitor 3,3'-oxybis[tetrahydrothiophene, 1,1,1',1'-tetraoxide.
Figure 3:
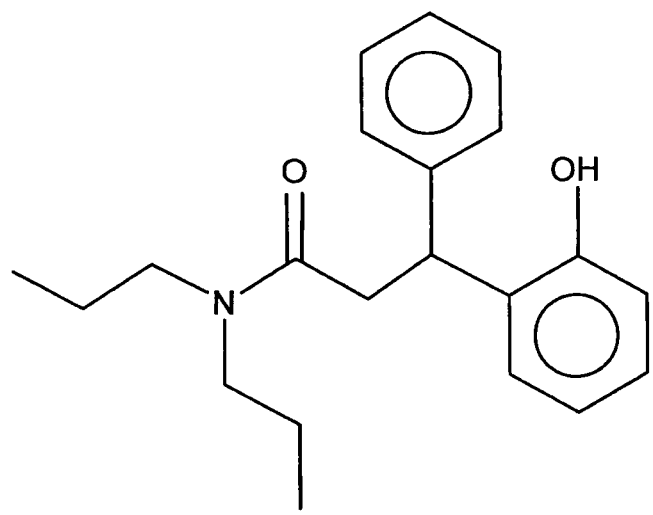
FIG. 3 illustrates the chemical structure of the Stat3 inhibitor 2-hydroxy-β-phenyl-N,N-dipropyl-benzenepropanamide, also known as 3-(2-Hydroxy-phenyl)-3-phenyl-N,N-dipropyl-propionamide.
Figure 4:
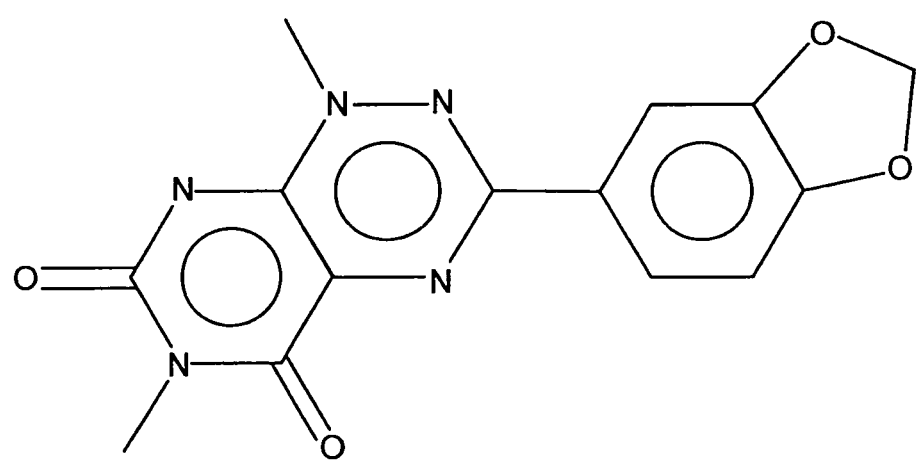
FIG. 4 illustrates the chemical structure of the Stat3 inhibitor 3-(1,3-benzodioxol-5-yl)-1,6-dimethyl-pyrimido[5,4-e]-1,2,4-triazine-5,7(1H,6H)-dione.

The present invention is directed to methods, kits and compositions for modulating the activity of Stat molecules (e.g., Stat1, Stat3 and Stat5). The compounds of the invention are useful for treating and/or preventing disorders characterized by Stat dysregulation, such as hyperproliferative disorders. The compounds of the present invention are also useful in culturing stem cells and treating ischemic conditions.

I. Definitions

As used herein, the term "cells having elevated Stat activity," refers to cells, e.g., in vitro or in vivo, in which Stat (e.g., Stat1, Stat3 and Stat5) is constitutively activated (e.g., phosphorylated) or cells in which Stat is activated for a greater percentage of time or at a higher level than is found in normal (i.e., non-diseased) cells. Similarly, "cells having reduced Stat activity," refers to cells, e.g., in vitro or in vivo, in which Stat (e.g., Stat1, Stat3 and Stat5) is not activated (e.g., phosphorylated) or cells in which Stat is not activated for a greater percentage of time or at a lower level than is found in normal (i.e., non-diseased) cells A "Stat activity" can be, without limitation, dimerization of Stat monomers, tyrosine and serine phosphorylation of Stat molecules, dimerized Stat bound to a Stat binding site, nuclear translocation, and transactivation of nucleic acid sequences operably linked to Stat binding sites (e.g., VEGF, BCL-X, MCL-1, CYCLIND1, SURVIVIN, CD46, and C-MYK). A Stat activator or agonist will enhance or increase a Stat activity while a Stat inhibitor or antagonist will decrease or prevent Stat activity. DNA-binding activity of Stat homodimers can be assessed using EMSA (Electrophoretic mobility shift assay). Dimerization of Stat monomers can be assessed using, without limitation, standard competitive binding assays and other protein-protein interaction assays, including FRET assays. Transactivation of a particular gene can be analyzed by expression profiling of the gene under inhibitory and non-inhibitory conditions. A "selective Stat activity" is a compound which results in a 25% or more difference in Stat activation (e.g., Stat1) or inhibition (e.g., Stat3),based on the luciferase assays described herein, in the presence versus the absence of the compound and results in less than a 12% difference in NF-κB activation or inhibition in the presence versus the absence of the compound. Assays for determining the "selective Stat activity" of a compound of the invention are described in Examples 1 and 2.

Stat activity can be evaluated by methods known in the art (e.g., phosphorylated-Stat specific antibodies) and described herein. U.S. Publication No. 2006/0247318, filed Feb. 24, 2006 and U.S. Publication No. 2005/0049299, filed Aug. 25, 2004, both of which are herein incorporated by reference in their entirety, describe assays for detecting Stat activity.

As used herein, a "hyperproliferative disorder" refers to cancer, neoplastic growth, hyperplastic or proliferative growth or a pathological state of abnormal cellular development and includes solid tumors, non-solid tumors, and any abnormal cellular proliferation, such as that seen in leukemia.

The terms "pharmacologically effective amount," "therapeutically effective amount", "pharmacologically effective dose" or simply "effective amount" refers to that amount of an agent effective to produce the intended pharmacological, therapeutic or preventive result. The pharmacologically effective amount results in the amelioration of one or more symptoms of a disorder, or prevents the advancement of a disorder, or causes the regression of the disorder. For example, with respect to the treatment of a hyperproliferative disorder, a therapeutically effective amount preferably refers to the amount of a therapeutic agent that decreases the rate of tumor growth, decreases tumor mass, decreases the number of metastases, increases time to tumor progression, or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%.

For example, with respect to the treatment of an ischemic injury, a therapeutically effective amount preferably refers to the amount of a therapeutic agent that prevents or limits tissue and/or cellular damage that would otherwise occur if treatment was not administered. The therapeutic agent decreases tissue and/or cellular damage by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100% compared to damage that occurs without the administration of a therapeutic agent of the invention.

The terms "anticancer agent" and "anticancer drug," as used herein, refer to any therapeutic agents (e.g., chemotherapeutic compounds and/or molecular therapeutic compounds), antisense therapies, radiation therapies, used in the treatment of hyperproliferative diseases such as cancer.

The terms "prevent," "preventing," and "prevention," as used herein with reference to a hyperproliferative disorder, refer to a decrease in the occurrence of pathological cells (e.g., hyperproliferative or neoplastic cells) in an animal. The prevention may be complete, e.g., the total absence of pathological cells in a subject. The prevention may also be partial, such that the occurrence of pathological cells in a subject is less than that which would have occurred without the present invention. In some embodiments, such terms refer to one, two, three or more results following the administration of one or more therapies: (1) a stabilization, reduction or elimination of the cancer cell population, (2) an increase in the length of remission, (3) a decrease in the recurrence rate of cancer, (4) an increase in the time to recurrence of cancer, and (6) an increase in the survival of the patient.

The terms "prevent," "preventing," and "prevention," as used herein with reference to ischemia, refer to a decrease in the occurrence of tissue and/or cellular damage in an animal. The prevention may be complete, e.g., the total absence of tissue damage in a subject. The prevention may also be partial, such that the occurrence of tissue damage in a subject is less than that which would have occurred without the therapeutic agent.

By "ischemia" we mean a condition where the blood flow to a tissue or organ is stopped. The stoppage may result from a blockage in the blood vessel supplying the tissue or organ (e.g. during a stroke, or deliberately during surgical procedures), or may result when the heart stops beating (e.g. a heart attack). Reperfusion is the term which describes the restarting of the supply of blood to the organ or tissue following ischemia.

As used herein, the term "candidate modulator" refers to a composition being evaluated for the ability to modulate a Stat activity. Candidate modulators can be natural or synthetic compounds, including, for example, small molecules, compounds contained in extracts of animal, plant, bacterial or fungal cells, as well as conditioned medium from such cells.

As used herein, "stem cell" refers to a cell with capability of multi-lineage differentiation and self-renewal, as well as the capability to regenerate tissue. Although stem cells are described mostly with respect to hematopoietic stem cells in the present application, the invention is not limited to such and may include stem cells of other origin, including but not limited to stem cells from liver, pancreas, neuron, and bone marrow mesenchymal stem cells.

The term "embryonic stem cell", as used herein refers to a stem cell obtained from a morula or a blastocyst stage of an embryo particularly in a preimplantation phase among the stem cells, and also called ES cell. Embryonic stem cells used in this specification may be of any animal species and, for example, include the embryonic stem cells of primates including a human, and mammals other than primates such as mammals and avian.

As used herein, the term an "undifferentiated state" refers to one or more cells in a state of having the ability of differentiating into one or more cells in a further differentiated state.

In a first aspect, the present invention is directed to a method for treating or preventing a hyperproliferative disorder in an individual. The method involves administering to an individual in need thereof a pharmacologically effective dose of pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-benzodioxol-5-yl)-1,6-dimethyl-pyrimido [5,4-e]-1,2,4-triazine-5,7(1H,6H)-dione or 3-(2-hydroxyphenyl)-3-phenyl-N,N-dipropylpropanamide. These compounds are known in the art and are readily available from commercial sources In another aspect, the invention is directed to a method of treating a hyperproliferative disorder in an individual comprising identifying a subject as in need of inhibition of Stat3 activity and administering a pharmacologically effective dose of a compound selected from the group consisting of pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 2-(1,8-Naphthyridin-2-yl)phenol, 3-(1,3-benzodioxol-5-yl)-1,6-dimethyl-pyrimido[5,4-e]-1,2,4-triazine-5, 7(1H,6H)-dione or 3-(2-hydroxyphenyl)-3-phenyl-N,N-dipropylpropanamide. In one embodiment, the subject is identified as in need of inhibition of Stat3 activity as the result of testing. The testing may involve any methods known in the art or described herein which detect a Stat3 activity. In a preferred embodiment, the subject has enhanced Stat3 activity.

In another aspect, the present invention is directed to a method for treating or preventing a hyperproliferative disorder in an individual. The method involves administering to an individual in need thereof a pharmacologically effective dose of a compound of Formula I:

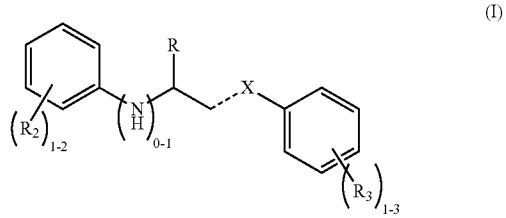

(I)

wherein

____ represents a single bond, a double bond, or a triple bond;

X is selected from the group consisting of —O—, —C—, —CH—, —CH$_2$—, and CR$_1$ where R$_1$ is 3-benzenesulfinic acid;

R is =O or H;

each R$_2$ is independently selected from the group consisting of H, —Cl, —NO$_2$, and —C(O)OCH$_3$, or two R$_2$ substituents are connected by —OCH$_2$CH$_2$O— to form a bicyclic ring; and each R$_3$ is independently selected from the group consisting of H, —Cl, —CH$_2$CH$_3$, —OH, —OCH$_3$, and —NO$_2$, and salts, esters or silanyl coordinated species thereof.

In yet another aspect, the present invention is directed to a method for treating or preventing a hyperproliferative disorder in an individual. The method involves administering to an individual in need thereof a pharmacologically effective dose of a compound of Formula II:

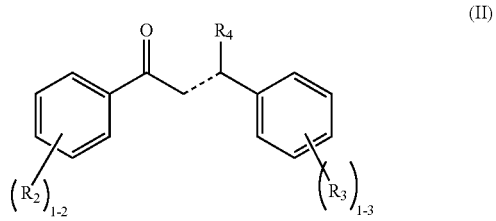

(II)

wherein

____ represents a double bond or a triple bond;

$R_4$ is H, 3-benzenesulfinic acid, or absent when ____ represents a triple bond;

R is =O or H;

each $R_2$ is H or two $R_2$ substituents are connected by —OCH$_2$CH$_2$O— to form a bicyclic ring; and each $R_3$ is independently selected from the group consisting of H, —CH$_2$CH$_3$, —OH, —OCH$_3$, and —NO$_2$ and salts, esters or silanyl coordinated species thereof.

In still another aspect, the present invention is directed to a method for treating or preventing a hyperproliferative disorder in an individual. The method involves administering to an individual in need thereof a pharmacologically effective dose of a compound of Formula III:

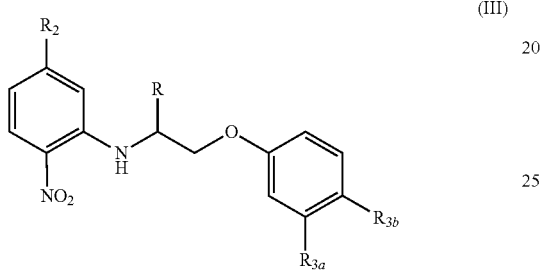

(III)

wherein

R is =O or H;

$R_2$ is H or —Cl;

$R_{3a}$ is H or —OCH$_3$; and $R_{3b}$ is H or Cl. and —NO$_2$ and salts, esters or silanyl coordinated species thereof.

In another aspect, the invention is directed to method for treating or preventing a hyperproliferative disorder in an individual, comprising administering to an individual in need thereof a pharmacologically effective dose a compound of Formula IV:

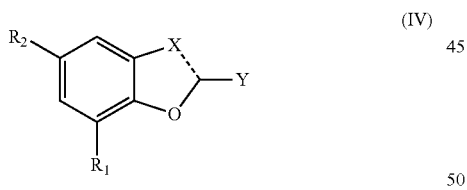

(IV)

wherein

____ represents a single or a double bond;

$R_1$ is H or —OCH$_3$;

$R_2$ is selected from the group consisting of H, —OCH$_3$, —(CH$_2$)$_2$C(O)NH(CH$_2$)$_2$OH and —NO$_2$;

X is —CR$_3$ or NR$_3$, and $R_3$ is H or —C(O)OCH$_2$CH$_3$; and

Y is 5-nitro-thiophen-2-yl or a phenyl, optionally substituted with one or more substituents selected from phenoxy or methoxy and salts, esters or silanyl coordinated species thereof.

In still another aspect, the present invention is directed to a method for treating or preventing a hyperproliferative disorder in an individual. The method involves administering to an individual in need thereof a pharmacologically effective dose of a compound selected from the group consisting of

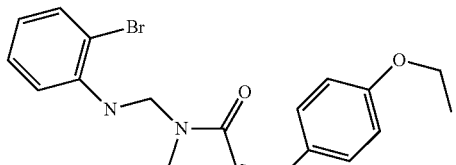

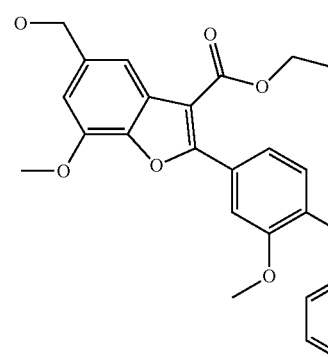

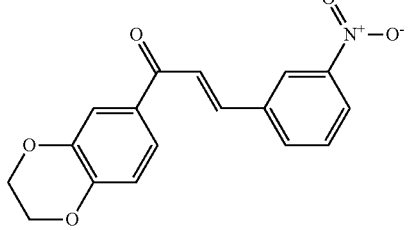

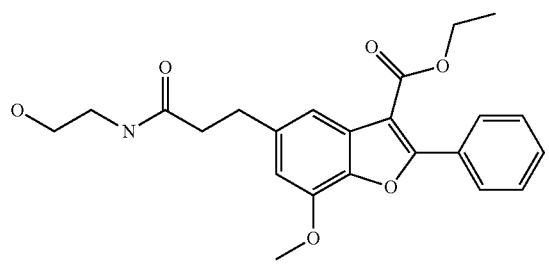

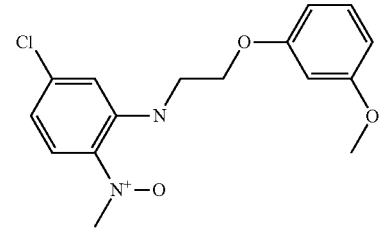

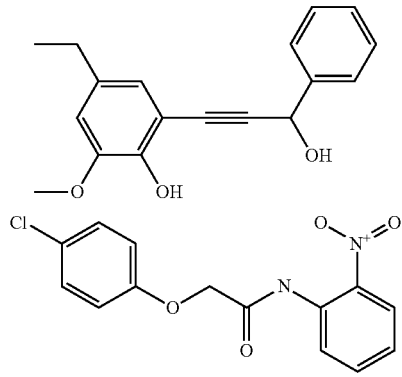

-continued

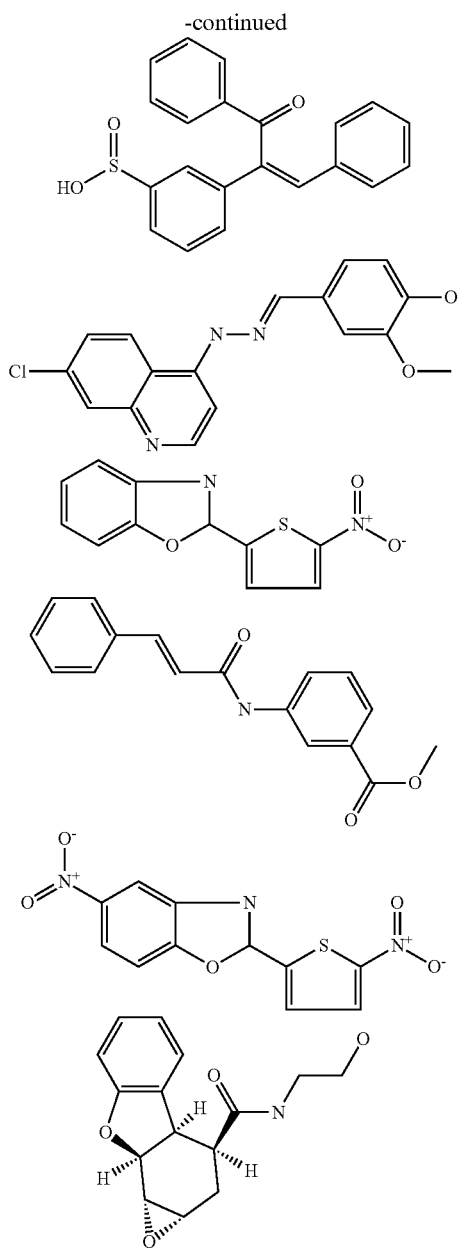

and salts or esters thereof.

The compounds for treating a hyperproliferative disorder may be administered individually or in combination. For example, the compound may be administered with an anti-cancer agent known in the art. Hyperproliferative disorders include cancer and solid tumors. Typical solid tumors for which the compounds are effective include breast cancer, melanoma, colon cancer, ovarian cancer, pancreatic cancer, lung cancer, hepatic cancer, head and neck cancer, prostate cancer and brain cancer. The compounds of the invention are also useful in the treatment of hematological cancers such as leukemia and multiple myeloma. Leukemia includes acute lymphoblastic leukemia, acute myelogenous leukemia, chronic myelogenous leukemia, Hodgkin's disease, non-Hodgkin's lymphoma, T-cell lymphoma, B-cell lymphoma and chronic lymphocytic leukemia.

In another aspect, the invention is directed to a method for inhibiting Stat3 activity in a cell. The method involves contacting the cell with an effective dose of pyrimethamine, pimozide, guanabenz acetate, alprenolol hydrochloride, nifuroxazide, solanine alpha, fluoxetine hydrochloride, ifosfamide, pyrvinium pamoate and moricizine hydrochloride, 3-(1,3-benzodioxol-5-yl)-1,6-dimethyl-pyrimido[5,4-e]-1,2,4-triazine-5,7(1H,6H)-dione or 3-(2-hydroxyphenyl)-3-phenyl-N,N-dipropylpropanamide and detecting a Stat3 activity in the cell. Stat3 activity includes Stat3 phosphorylation, Stat3 dimerization, Stat3 binding to a polynucleotide having a Stat3 binding site, activation of a Stat3 responsive gene and Stat3 nuclear translocation. Suitable Stat3 responsive genes include Egr-1, JunB, cyclin D1, Mcl-1, Bcl-2, Bcl-xl and survivin. In some embodiments, the cell is transfected with a nucleic acid encoding Stat3.

In yet another aspect, the invention is directed to a method for inducing Stat3 activity in a cell. The method involves contacting the cell with an effective dose of mebendazole, nocodazole, nortriptyline hydrochloride, zimelidine dihydrochloride monohydrate, adenosine 5'-monophosphate monohydrate, promazine hydrochloride, podophyllotoxin, ribavirin, deptropine citrate, or 4-(3,4-Dimethyl-phenoxy)-N-hydroxy-benzamidine and detecting Stat3 activity in the cell. These compounds are known in the art and are readily available from commercial sources. Stat3 activity includes Stat3 phosphorylation, Stat3 dimerization, Stat3 binding to a polynucleotide having a Stat3 binding site, activation of a Stat3 responsive gene and Stat3 nuclear translocation. Suitable Stat3 responsive genes include Egr-1, JunB, cyclin D1, Mcl-1, Bcl-2, Bcl-xl and survivin. In some embodiments, the cell is transfected with a nucleic acid encoding Stat3.

In yet another aspect, the invention is directed to a method of inducing Stat 1 activity by contacting a cell with an effective dose a compound of Formula I, II, III, IV or a compound selected from Table 1. Stat1 activity includes Stat1 phosphorylation, Stat1 dimerization, Stat1 binding to a polynucleotide comprising a Stat1 binding site, activation of a Stat1 responsive gene and Stat1 nuclear translocation. Suitable Stat1 responsive genes include caspase-1, Fas and FasL In some embodiments, the cell is transfected with a nucleic acid encoding Stat1.

In another aspect, the invention is directed to treating or preventing an ischemic injury in an individual. The method involves administering to an individual in need thereof a pharmacologically effective dose of mebendazole, nocodazole, nortriptyline hydrochloride, zimelidine dihydrochloride monohydrate, adenosine 5'-monophosphate monohydrate, promazine hydrochloride, podophyllotoxin, ribavirin, deptropine citrate, or 4-(3,4-Dimethyl-phenoxy)-N-hydroxy-benzamidine. The ischemic injury may result from disorders which include atherosclerosis, myocardial infraction, stroke, vascular occlusion or cardiac arrest.

In still another aspect of the invention, the invention is directed to a method for maintaining a stem cell in an undifferentiated state. The method includes contacting the stem cell with a pharmacologically effective dose of mebendazole, nocodazole, nortriptyline hydrochloride, zimelidine dihydrochloride monohydrate, adenosine 5'-monophosphate monohydrate, promazine hydrochloride, podophyllotoxin, ribavirin, or 4-(3,4-Dimethyl-phenoxy)-N-hydroxy-benzamidine. Both murine and human stem cells are suitable for practicing the invention.

The invention is also directed to a cell (cell lines deposited under ATCC Nos. [ ], deposited on) for screening Stat-3 modulators.

In still another aspect, the invention is directed to a method for screening for a Stat-3 activator. The method includes incubating a cell, having a Stat3 regulatory element operatively linked to a reporter construct, in the presence and absence of a candidate modulator, and detecting a signal from the reporter construct. An increase in the signal in the presence of the candidate modulator when compared with the signal in the absence of said candidate modulator is indicative of a Stat-3 activator.

In yet another aspect, the invention is directed to a method for screening for a Stat-3 inhibitor. The method involves incubating a cell, having a Stat3 regulatory element operatively linked to a reporter construct, in the presence and absence of a candidate modulator and detecting a signal from the reporter construct. A decrease in the signal in the presence of the candidate modulator when compared with the signal in the absence of the candidate modulator is indicative of a Stat-3 inhibitor.

The invention is also directed to a cell (cell lines deposited under ATCC Nos. [ ], deposited on) for screening Stat-1 modulators.

In still another aspect, the invention is directed to a method for screening for a Stat-1 activator. The method includes incubating a cell (ATCC Nos. [ ]) in the presence and absence of a candidate modulator, and detecting a signal from the reporter molecule. The cell has a Stat1 regulatory element operatively linked to a reporter molecule. An increase in the signal in the presence of the candidate modulator when compared with the signal in the absence of said candidate modulator is indicative of a Stat-1 activator.

In yet another aspect, the invention is directed to a method for screening for a Stat-1 inhibitor. The method involves incubating a cell in the presence and absence of a candidate modulator and detecting a signal from the reporter molecule. The cell has a Stat1 regulatory element operatively linked to a reporter molecule. A decrease in the signal in the presence of the candidate modulator when compared with the signal in the absence of the candidate modulator is indicative of a Stat-1 inhibitor.

The invention is also directed to a cell (cell lines deposited under ATCC Nos. [ ], deposited on) for screening Stat-5 modulators.

In still another aspect, the invention is directed to a method for screening for a Stat-5 activator. The method includes incubating a cell (ATCC Nos. [ ]) in the presence and absence of a candidate modulator, and detecting a signal from the reporter molecule. The cell has a Stat1 regulatory element operatively linked to a reporter molecule. An increase in the signal in the presence of the candidate modulator when compared with the signal in the absence of said candidate modulator is indicative of a Stat-5 activator.

In yet another aspect, the invention is directed to a method for screening for a Stat-5 inhibitor. The method involves incubating a cell in the presence and absence of a candidate modulator and detecting a signal from the reporter molecule. The cell has a Stat5 regulatory element operatively linked to a reporter molecule. A decrease in the signal in the presence of the candidate modulator when compared with the signal in the absence of the candidate modulator is indicative of a Stat-5 inhibitor.

In a further aspect, the invention is directed to kits and compositions for practicing any of the methods of the invention.

II. Stat Molecules

Stats are present in the cytoplasm of cells under basal conditions. When activated by tyrosine phosphorylation, Stats form dimmers and translocate to the nucleus where they can bind specific nine base pair sequences in the regulatory regions of target genes, thereby activating transcription. A variety of tyrosine kinases, including polypeptide growth factor receptors, Src family members, and other kinases can catalyze this phosphorylation (4). While tyrosine phosphorylation is essential for their activation, Stats can also be phosphorylated on unique serine residues as well. Although this is not sufficient to induce dimerization and DNA binding, Stat serine phosphorylation modulates the transcriptional response mediated by a tyrosine-phosphorylated Stat dimer, and may mediate distinct biological effects (Zhang X, et al. Science 1995; 267:1990-1994; Wen Z, et al. Cell 1995; 82:241-250; Kumar A, et al. Science 1997; 278:1630-1632.) Stats have been found to function inappropriately in many human malignancies (Alvarez J V, et al., Cancer Res 2005; 65(12):5054-62; Frank D A, et al. Cancer Treat. Res. 2003; 115:267-291; Bowman T, et al. Oncogene 2000; 19(21):2474-88).

Stat3

Stat3 is activated in several human tumors, including common epithelial cancers such as cancer of the breast, prostate, lung, pancreas, and ovary; hematologic cancers such as multiple myeloma, and acute leukemias; and diverse tumors such as melanoma and gliomas (Frank D A, et al. Cancer Treat. Res. 2003; 115:267-291). Many of the target genes of Stat3 code for proteins involved in cell survival, cell cycle progression, differentiation inhibition, invasion, and angiogenesis, all of the essential processes necessary for tumor formation and maintenance (Alvarez J V, et al., Cancer Res 2005; 65(12):5054-62). Inhibition of Stat3 function in cancer cells associated with enhanced Stat3 activity leads to a loss of proliferation and survival of the cancer cells (Frank D A. Curr. Cancer Therapy Reviews 2006; 2:57-65). Despite the central role that Stat3 plays in these diverse processes in tumor cell biology, loss of Stat3 function in normal adult cells has few if any serious consequences, and may in fact decrease the ability of a cell to become transformed. Furthermore, by decreasing a variety of pro-survival pathways, Stat3 inhibition may be particularly effective in sensitizing cancer cells to other modalities of treatment such as chemotherapy and radiation. In one embodiment, the current invention contemplates administering a Stat3 inhibitor to treat a hyperproliferative disorder.

In another embodiment, the invention is directed to treating or preventing an ischemic injury in an individual. Stat3 activation has been implicated in the protection of tissue form ischemic injury (Hilfiker-Kleiner, D. Circulation Research. 95:187-195 (2004). It was shown that Stat3 deficient mice had enhanced susceptibility to myocardial ischemia/reperfusion injury and infraction while activating Stat3 enhanced cell survival following exposure to simulated ischemia/reperfusion injury (Hilfiker-Kleiner, D. Circulation Research. 95:187-195 (2004); Stephanou, A. J. Cell. Mol. Med. 8(4): 519-525 (2004).

In one aspect of the invention, the invention is directed to a method for maintaining a stem cell in an undifferentiated state. Stat3 activation has also been shown to aid in maintaining stem cell pluripotentcy. For example, Stat3 activation is sufficient to maintain an undifferentiated state of mouse embryonic stem cells (Matsuda et al. EMBO Journal, 18, 15, 4261-4269 (1999)). Similarly, Niwa et al., (Genes & Development, 12, 13, 2048-2060 (1998)) teaches that self-renewal of pluripotent embryonic stem cells is mediated via activation of Stat3.

Stat1

Activated Stat1 functions much like a tumor suppressor gene. Whereas inappropriate or constitutive Stat3 activation appears to correlate directly with tumor development, Stat1 plays a reciprocal role. Stat1 opposes many of the effects mediated by Stat3, e.g., gene expression. Under physiologic conditions Stat1 activation mediates expression of inhibitors of cyclin-dependent kinases and represses genes necessary for cell cycle entry (Ramana C V, et al. Embo J 2000; 19:263-72). Furthermore, Stat1 activation can repress pro-survival genes (Stephanou A, et al. Cell Death Differ 2000; 7(3):329-30) and trigger apoptosis (Sironi J J, et al. J. Biol. Chem. 2004; 279:4066-74; Battle T E, et al. Curr. Mol. Med. 2002; 2:381-392). Consequently, Stat1 activation may be important in mediating the therapeutic effect of biological therapies for cancer (Battle T E, et al. Clin. Cancer Res. 2003; 9:2166-72) and the induced differentiation of tumor cells. Furthermore, loss of Stat1 enhances metastasis and angiogenesis in murine systems. Similarly, loss of the ability to activate Stat1 has been found to occur in lung cancer and prostate cancer, whereas increased phosphorylation and DNA binding activity of Stat1 is associated with decreased relapse and increased survival in patients with newly diagnosed breast cancer. In one embodiment, the current invention contemplates administering a Stat1 activator to treat a hyperproliferative disorder.

Stat5

Stat5 has also been found to mediate tumorigenesis, particularly in hematopoietic cells (Lin T S, et al. Oncogene 2000; 19:2496-2504). Stat5 is phosphorylated by a number of fusion kinases formed as a result of chromosomal translocations in leukemia. Prototypically, Stat5 is phosphorylated by Bcr-Abl in chronic myelogenous leukemia (CML), and is necessary for the transforming ability of this kinase. In many other leukemias and murine leukemia models Stat5 is similarly necessary for transformation.

Stat5 has been found to be activated constitutively in many patients with breast cancer (Cotarla I, et al. Int. J. Cancer 2004; 108:665-671). However, just as prolactin can promote differentiation of mammary epithelium, activated Stat5 may also promote the development of more differentiated malignancies. In fact Stat5 activation in breast cancer has been associated with a favorable prognosis. Thus, whereas it would be useful to inhibit Stat5 function in leukemias, it might be advantageous to accentuate its actions in breast cancer.

III. Stat Modulators

The compounds of the invention are useful in the selective modulation of Stat molecules (e.g., Stat1, Stat3, Stat5). The compounds of the invention include the Stat3 inhibitors: pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-benzodioxol-5-yl)-1,6-dimethyl-pyrimido[5,4-e]-1,2,4-triazine-5,7(1H,6H)-dione, 2-(1,8-Naphthyridin-2-yl)phenol, 3-(2-hydroxyphenyl)-3-phenyl-N,N-dipropylpropanamide as well as any derivatives of these compounds or analogues thereof. These compounds are commercially available through various sources.

Many of the compounds of the invention are currently prescribed for various disorders. For example, pyrimethamine is sold under the brand name Daraprim for the treatment of protozoal infections including malaria and *Toxoplasma gondii* infections. Pimozide is sold as Orap to control tics caused by Tourette's disorder. Guanabenz Acetate is an alpha agonist used to treat high blood pressure. Alprenolol hydrochloride is a beta-receptor blocking agent used for the treatment of cardiac arrhythmias. Nifuroxazide is an orally administered anti-diarrehal that is sold under numerous brand names including, Akabar, Antinal and Bacifurane. Fluoxetine hydrochloride is sold under the brand name Prozac and is a psychotropic drug that is administered orally. Ifosfamide is an intravenous drug sold under the brand name Mitoxana for the treatment of testicular cancer, cervical cancer, Ewing's sarcoma, and non-Hodgkin's lymphoma. Pyrvinium pamoate is sold under the brand name Vanquin for the treatment of pinworms. Moricizine hydrochloride is sold under the brand name Ethmozine as an orally active antiarrhythmic drug.

The compounds of the invention also include activators of Stat3. Stat3 activators include: mebendazole, nocodazole, nortriptyline hydrochloride, zimelidine dihydrochloride monohydrate, adenosine 5'-monophosphate monohydrate, promazine hydrochloride, podophyllotoxin, ribavirin, deptropine citrate, and 4-(3,4-Dimethyl-phenoxy)-N-hydroxybenzamidine.

The Stat3 activators are all readily available in the art. Mebendazole is sold under the brand names Ovex, Vermox, Antiox and Pripsen and prescribed for the treatment of pinworms, roundworms and hookworms. Nocodazole is an antineoplastic agent which exerts its effect in cells by depolymerizing microtubules. Nortriptyline hydrochloride is sold under the brand name Aventyl and Pamelor and is used for the treatment of depression and nocturnal enuresis. Zimelidine dihydrochloride monohydrate is sold under the brand name Normud and Zelmid for the treatment of depression. Promazine hydrochloride is prescribed for treating agitation and restlessness. Podophyllotoxin is a topical cream that is prescribed for the treatment of viral warts. Ribavirin is sold under the brand names Copegus' Rebetol, Ribasphere, Vilona and Virazole and used orally or in aerosol form as an anti-viral. Deptropine citrate is an antihistamine for the treatment of respiratory-tract disorders.

In another embodiment of the invention, the compound is a Stat1 activator. Suitable Stat1 activators include a compound of Formula I:

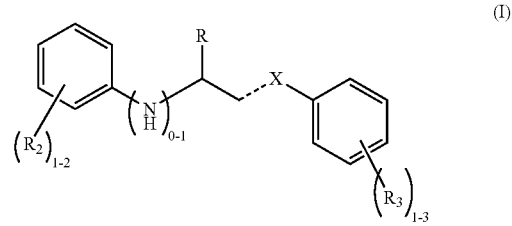

wherein

---- represents a single bond, a double bond, or a triple bond;

X is selected from the group consisting of —O—, —C—, —CH—, —CH$_2$—, and CR$_1$ where R$_1$ is 3-benzenesulfinic acid;

R is =O or H;

each R$_2$ is independently selected from the group consisting of H, —Cl, —NO$_2$, and —C(O)OCH$_3$, or two R$_2$ substituents are connected by —OCH$_2$CH$_2$O— to form a bicyclic ring; and each R$_3$ is independently selected from the group consisting of H, —Cl, —CH$_2$CH$_3$, —OH, —OCH$_3$, and —NO$_2$, and salts, esters or silanyl coordinated species thereof.

In another embodiment, the Stat1 activator is a compound of Formula II:

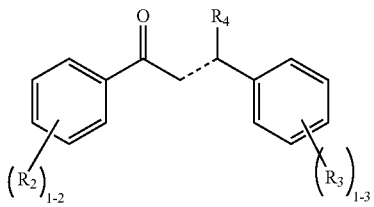

(II)

wherein
\_\_\_\_ represents a double bond or a triple bond;
$R_4$ is H, 3-benzenesulfinic acid, or absent when \_\_\_\_ represents a triple bond;
R is =O or H;
each $R_2$ is H or two $R_2$ substituents are connected by —OCH$_2$CH$_2$O— to form a bicyclic ring; and
each $R_3$ is independently selected from the group consisting of H, —CH$_2$CH$_3$, —OH, —OCH$_3$, and —NO$_2$ and salts, esters or silanyl coordinated species thereof.

In yet another embodiment, the Stat1 activator is a compound of Formula III:

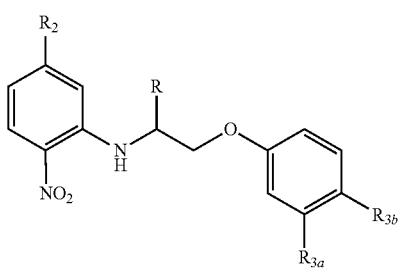

(III)

wherein
R is =O or H;
$R_2$ is H or —Cl;
$R_{3a}$ is H or —OCH$_3$; and
$R_{3b}$ is H or Cl. and —NO$_2$ and salts, esters or silanyl coordinated species thereof.

In still another embodiment, the Stat1 activator is a compound of Formula IV:

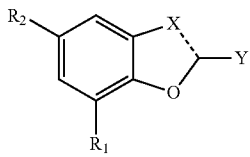

(IV)

wherein
\_\_\_\_ represents a single or a double bond;
$R_1$ is H or —OCH$_3$;
$R_2$ is selected from the group consisting of H, —OCH$_3$, —(CH$_2$)$_2$C(O)NH(CH$_2$)$_2$OH and —NO$_2$;
X is —CR$_3$ or NR$_3$, and R$_3$ is H or —C(O)OCH$_2$CH$_3$; and
Y is 5-nitro-thiophen-2-yl or a phenyl, optionally substituted with one or more substituents selected from phenoxy or methoxy and salts, esters or silanyl coordinated species thereof.

In particular embodiments, the compounds of the invention may be selected from the exemplary compound listing shown below (Table 1). Importantly, it should be noted that the tabular listing below is used merely as a convenience, and each compound below should be considered a separate embodiment of the invention:

TABLE 1

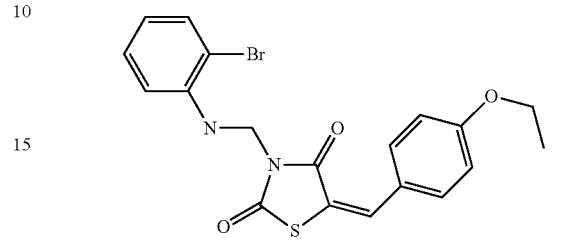

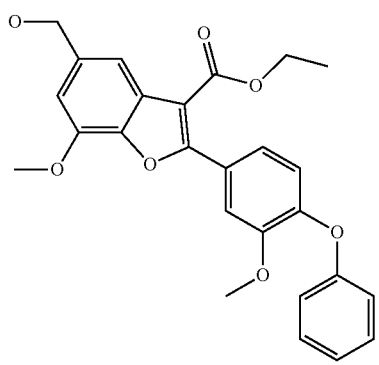 [SMILES: CCOC(=O)c1c(-c2ccc(Oc3ccccc3)c(OC)c2)oc2c(OC)cc(CO)cc12]

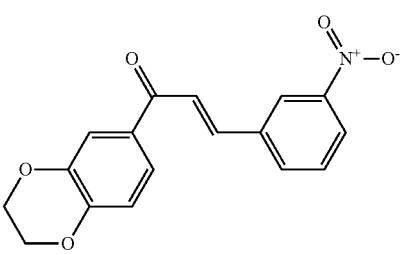 [SMILES: O=C(/C=C/c1cccc([N+](=O)[O-])c1)c1ccc2c(c1)OCCO2]

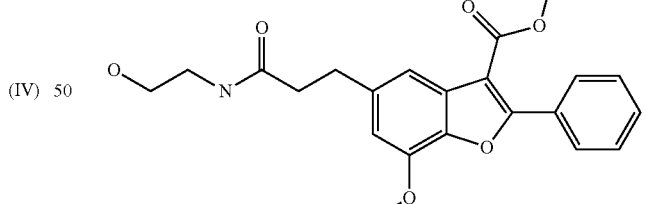

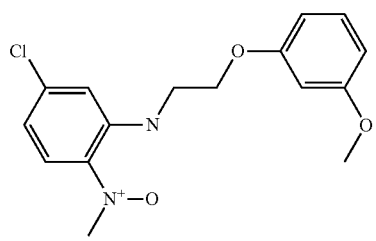 [SMILES: COc1cccc(OCCNc2cc(Cl)ccc2[NH+](C)O)c1]

TABLE 1-continued

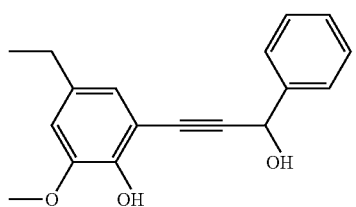 [SMILES: CCc1cc(C#CC(O)c2ccccc2)c(O)c(OC)c1]

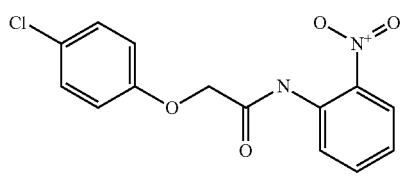

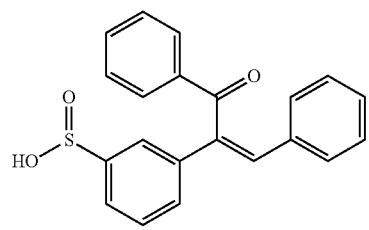 [SMILES: O=C(/C(=C\c1ccccc1)c1cccc(S(=O)O)c1)c1ccccc1]

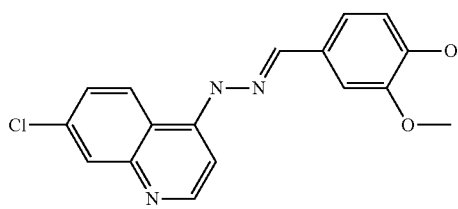 [SMILES: COc1cc(/C=N/Nc2ccnc3cc(Cl)ccc23)ccc1O]

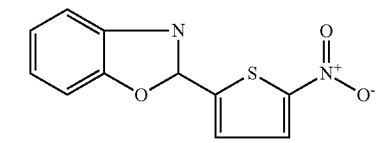 [SMILES: O=[N+]([O-])c1ccc(C2Nc3ccccc3O2)s1]

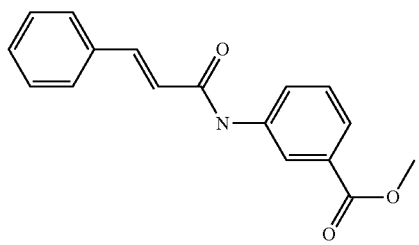 [SMILES: COC(=O)c1cccc(NC(=O)/C=C/c2ccccc2)c1]

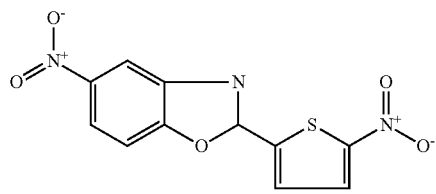 [SMILES: O=[N+]([O-])c1ccc2c(c1)NC(c1ccc([N+](=O)[O-])s1)O2]

TABLE 1-continued

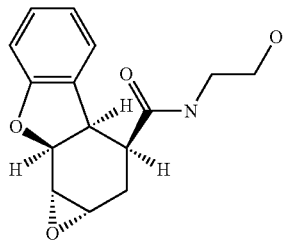 [SMILES: O=C(NCCO)[C@H]1C[C@@H]2O[C@@H]2[C@H]2Oc3ccccc3[C@H]21]

and salts, esters or silanyl associated species thereof (e.g., wherein silanyl associated species describes species that are associated to a compound of the present invention by being present in a measurable amount and administered therewith, e.g., $(CH_3)_3C$—Si—$(CH_3)_2$—$CH_2OH$).

IV. Stat Modulators for the Treatment and Prevention of Hyperproliferative Disorders A. Hyperproliferative Disorders In one aspect, the present invention is directed to a method of treating or preventing a hyperproliferative disorder in an individual in need of such treatment, comprising the step of administering a pharmacologically effective dose of compound of a compound of the invention to the individual. Representative compounds for the treatment of hyperproliferative disorder include: pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(1,3-benzodioxol-5-yl)-1,6-dimethyl-pyrimido[5,4-e]-1,2,4-triazine-5,7(1H,6H)-dione, 2-(1,8-Naphthyridin-2-yl)phenol, 3-(2-hydroxyphenyl)-3-phenyl-N,N-dipropylpropanamide as well as any derivatives of these compounds or analogues thereof.

Although Stat-3 inhibitors may be useful to treat any hyperproliferative disorder, it is contemplated that this method will be particularly useful when the individual has a hyperproliferative disorder characterized by an elevated Stat3 activity.

Hyperproliferative disorders include cancerous disease states. Cancerous disease states may be categorized as pathologic, i.e., characterizing or constituting a disease state, e.g., malignant tumor growth, or may be categorized as non-pathologic, i.e., a deviation from normal but not associated with a disease state, e.g., cell proliferation associated with wound repair. The term is meant to include all types of cancerous growths or oncogenic processes, metastatic tissues or malignantly transformed cells, tissues, or organs, irrespective of histopathologic type or stage of invasiveness. The term "cancer" includes malignancies of the various organ systems, such as those affecting lung, breast, thyroid, lymphoid, gastrointestinal, and genito-urinary tract, as well as adenocarcinomas which include malignancies such as most colon cancers, renal-cell carcinoma, prostate cancer and/or testicular tumors, non-small cell carcinoma of the lung, cancer of the small intestine and cancer of the esophagus. The term "carcinoma" is art recognized and refers to malignancies of epithelial or endocrine tissues including respiratory system carcinomas, gastrointestinal system carcinomas, genitourinary system carcinomas, testicular carcinomas, breast carcinomas, prostatic carcinomas, endocrine system carcinomas, and melanomas. Exemplary carcinomas include those forming from tissue of the cervix, lung, prostate, breast, head and neck, colon and ovary. The term "carcinoma" also includes carcinosarcomas, e.g., which include malignant tumors composed of carcinomatous and sarcomatous tissues. An "adenocarcinoma" refers to a carcinoma derived from glandular tissue or in which the tumor cells form recognizable glandular structures. The term "sarcoma" is art recognized and refers to malignant tumors of mesenchymal derivation.

In one embodiment of the invention, the compounds can be used to treat or prevent a variety of hyperproliferative disorders. Preferentially, the compounds of the invention are used to treat a cancer with elevated Stat3 activity (e.g., breast cancer, colon cancer and prostate cancer). In a further embodiment, the invention is used to treat a solid tumor. In a preferred embodiment, the solid tumor is breast cancer, melanoma, colon cancer, ovarian cancer, pancreatic cancer, lung cancer, hepatic cancer, head and neck cancer, prostate cancer and brain cancer. In another embodiment, the hyperproliferative disorder is a hematological cancer such as leukemia or multiple myeloma. Leukemia includes acute lymphoblastic leukemia, acute myelogenous leukemia, chronic myelogenous leukemia, Hodgkin's disease, non-Hodgkin's lymphoma, T-cell lymphoma, B-cell lymphoma and chronic lymphocytic leukemia.

In another aspect, the invention is directed to a method of treating a hyperproliferative disorder in an individual comprising identifying a subject as in need of inhibition of Stat3 activity and administering a pharmacologically effective dose of a compound selected from the group consisting of pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 3-(2-Hydroxy-phenyl)-3-phenyl-N,N-dipropylpropionamide, 3-(1,3-benzodioxol-5-yl)-1,6-dimethyl-pyrimido[5,4-e]-1,2,4-triazine-5,7(1H,6H)-dione or 3-(2-hydroxyphenyl)-3-phenyl-N,N-dipropylpropanamide. The subject in need of inhibition of Stat3 will generally display enhanced Stat3 activity as described herein. It is readily apparent to one of ordinary skill in the art, based on the teachings herein, how to determine whether an individual has enhanced Stat3 activity.

The compounds of the invention can also be used to treat additional hyperproliferative disorders including but not limited to, cancer of the head, neck, eye, skin, mouth, throat, esophagus, chest, bone, lung, colon, sigmoid, rectum, stomach, prostate, ovary, testicle, kidney, liver, pancreas, brain, intestine, heart or adrenals (for a review of such disorders, see Fishman et al., 1985, Medicine, 2d Ed., J.B. Lippincott Co., Philadelphia).

B. Formulations for the Treatment of a Hyperproliferative Disorder

The present invention provides compositions that are suitable for veterinary and/or human administration (e.g., pharmaceutical compositions). The pharmaceutical compositions of the present invention can be in any form that allows for the composition to be administered to a subject, said subject preferably being an animal, including, but not limited to a human, mammal, or non-human animal, such as a cow, horse, sheep, pig, fowl, cat, dog, mouse, rat, rabbit, guinea pig, etc., and is more preferably a mammal, and most preferably a human.

The following compounds are preferably administered in the form as they are currently prescribed: pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3,3'-oxybis[tetrahydrothiophene, 1,1,1',1'-tetraoxide], 2-(1,8-Naphthyridin-2-yl)phenol, 3-(1,3-benzodioxol-5-yl)-1,6-dimethyl-pyrimido[5,4-e]-1,2,4-triazine-5,7(1H,6H)-dione, 3-(2-hydroxyphenyl)-3-phenyl-N,N-dipropylpropanamide as well as any derivatives of these compounds or analogues thereof.

Many of the compounds of the invention are currently prescribed for various disorders. For example, pyrimethamine is sold under the brand name Daraprim for the treatment of protozoal infections including malaria and *Toxoplasma gondii* infections. Pimozide is sold as Orap to control tics caused by Tourette's disorder. Guanabenz Acetate is an alpha agonist used to treat high blood pressure. Alprenolol hydrochloride is a beta-receptor blocking agent used for the treatment of cardiac arrhythmias. Nifuroxazide is an orally administered anti-diarrheal that is sold under numerous brand names including, Akabar, Antinal and Bacifurane. Fluoxetine hydrochloride is sold under the brand name Prozac and is a psychotropic drug that is administered orally. Ifosfamide is an intravenous drug sold under the brand name Mitoxana for the treatment of testicular cancer, cervical cancer, Ewing's sarcoma, and non-Hodgkin's lymphoma. Pyrvinium pamoate is sold under the brand name Vanquin for the treatment of pinworms. Moricizine hydrochloride is sold under the brand name Ethmozine as an orally active antiarrhythmic drug.

The formulation of a compound of the invention used in the prophylactic and/or therapeutic regimens which will be effective in the prevention, treatment, and/or management of cancer can be based on the currently available formulation. Alternatively the compounds can be reformulated based on knowledge within the art and the teachings herein. For example, the compound may be in the form of a solid, liquid or gas (aerosol). Typical routes of administration may include, without limitation, oral, topical, parenteral, sublingual, rectal, vaginal, ocular, intradermal, intratumoral, intracerebral, intrathecal, and intranasal. Parenteral administration includes subcutaneous injections, intravenous, intramuscular, intraperitoneal, intrapleural, intrasternal injection or infusion techniques. In a specific embodiment, the compositions are administered parenterally. In a more specific embodiment, the compositions are administered intravenously. Pharmaceutical compositions of the invention can be formulated so as to allow a compound of the invention to be bioavailable upon administration of the composition to a subject. Compositions can take the form of one or more dosage units, where, for example, a tablet can be a single dosage unit, and a container of a compound of the invention in aerosol form can hold a plurality of dosage units.

Materials used in preparing the pharmaceutical compositions can be non-toxic in the amounts used. It will be evident to those of ordinary skill in the art that the optimal dosage of the active ingredient(s) in the pharmaceutical composition will depend on a variety of factors. Relevant factors include, without limitation, the type of subject (e.g., human), the overall health of the subject, the type of cancer the subject is in need of treatment of, the use of the composition as part of a multi-drug regimen, the particular form of the compound of the invention, the manner of administration, and the composition employed.

The pharmaceutically acceptable carrier or vehicle may be particulate, so that the compositions are, for example, in tablet or powder form. The carrier(s) can be liquid, with the compositions being, for example, an oral syrup or injectable liquid. In addition, the carrier(s) can be gaseous, so as to provide an aerosol composition useful in, e.g., inhalatory administration.

The term "carrier" refers to a diluent, adjuvant or excipient, with which a compound of the invention is administered. Such pharmaceutical carriers can be liquids, such as water and oils, including those of petroleum, animal, vegetable or synthetic origin, such as peanut oil, soybean oil, mineral oil, sesame oil and the like. The carriers can be saline, gum acacia, gelatin, starch paste, talc, keratin, colloidal silica, urea, and the like. In addition, auxiliary, stabilizing, thickening, lubricating and coloring agents can be used. In one embodiment, when administered to a subject, the compounds of the invention and pharmaceutically acceptable carriers are sterile. Water is a preferred carrier when the compound of the invention is administered intravenously. Saline solutions and aqueous dextrose and glycerol solutions can also be employed as liquid carriers, particularly for injectable solutions. Suitable pharmaceutical carriers also include excipients such as starch, glucose, lactose, sucrose, gelatin, malt, rice, flour, chalk, silica gel, sodium stearate, glycerol monostearate, talc, sodium chloride, dried skim milk, glycerol, propylene, glycol, water, ethanol and the like. The present compositions, if desired, can also contain minor amounts of wetting or emulsifying agents, or pH buffering agents.

The composition may be intended for oral administration, and if so, the composition is preferably in solid or liquid form, where semi-solid, semi-liquid, suspension and gel forms are included within the forms considered herein as either solid or liquid.

As a solid composition for oral administration, the composition can be formulated into a powder, granule, compressed tablet, pill, capsule, chewing gum, wafer or the like form. Such a solid composition typically contains one or more inert diluents. In addition, one or more of the following can be present: binders such as ethyl cellulose, carboxymethylcellulose, microcrystalline cellulose, or gelatin; excipients such as starch, lactose or dextrins, disintegrating agents such as alginic acid, sodium alginate, Primogel, corn starch and the like; lubricants such as magnesium stearate or Sterotex; glidants such as colloidal silicon dioxide; sweetening agents such as sucrose or saccharin, a flavoring agent such as peppermint, methyl salicylate or orange flavoring, and a coloring agent.

When the pharmaceutical composition is in the form of a capsule, e.g., a gelatin capsule, it can contain, in addition to materials of the above type, a liquid carrier such as polyethylene glycol, cyclodextrin or a fatty oil.

The pharmaceutical composition can be in the form of a liquid, e.g., an elixir, syrup, solution, emulsion or suspension. The liquid can be useful for oral administration or for delivery by injection. When intended for oral administration, a composition can comprise one or more of a sweetening agent, preservatives, dye/colorant and flavour enhancer. In a composition for administration by injection, one or more of a surfactant, preservative, wetting agent, dispersing agent, suspending agent, buffer, stabilizer and isotonic agent can also be included.

The liquid compositions of the invention, whether they are solutions, suspensions or other like form, can also include one or more of the following: sterile diluents such as water for injection, saline solution, preferably physiological saline, Ringer's solution, isotonic sodium chloride, fixed oils such as synthetic mono or diglycerides which can serve as the solvent or suspending medium, polyethylene glycols, glycerin, cyclodextrin, propylene glycol or other solvents; antibacterial agents such as benzyl alcohol or methyl paraben; antioxidants such as ascorbic acid or sodium bisulfite; chelating agents such as ethylenediaminetetraacetic acid; buffers such as acetates, citrates or phosphates and agents for the adjustment of tonicity such as sodium chloride or dextrose. A parenteral composition can be enclosed in an ampoule, a disposable syringe or a multiple-dose vial made of glass, plastic or other material. Physiological saline is a preferred adjuvant. An injectable composition is preferably sterile.

The pharmaceutical compositions comprise an effective amount of a compound of the invention such that a suitable dosage will be obtained. The pharmaceutical compositions may comprise the known effective amount of the compounds as currently prescribed for their respective disorders.

Typically, the effective amount is at least 0.01% of a compound of the invention by weight of the composition. When intended for oral administration, this amount can be varied to be between 0.1% and 80% by weight of the composition. Preferred oral compositions can comprise from between 4% and 50% of the compound of the invention by weight of the composition. Preferred compositions of the present invention are prepared so that a parenteral dosage unit contains from between 0.01% and 2% by weight of the compound of the invention.

The route of administration compound of the invention used in the prophylactic and/or therapeutic regimens which will be effective in the prevention, treatment, and/or management of a hyperproliferative disorder can be based on the currently prescribed routes of administration as well as assessed by methods disclosed herein. The compounds of the invention can be administered by any convenient route, for example, by infusion or bolus injection, by absorption through epithelial or mucocutaneous linings (e.g., oral mucosa, rectal and intestinal mucosa, etc.). Administration can be systemic or local. Various delivery systems are known, e.g., microparticles, microcapsules, capsules, etc., and may be useful for administering a compound of the invention. In certain embodiments, more than one compound of the invention is administered to a subject. Methods of administration may include, but are not limited to, oral administration and parenteral administration; parenteral administration including, but not limited to, intradermal, intramuscular, intraperitoneal, intravenous, subcutaneous; intranasal, epidural, sublingual, intranasal, intracerebral, intraventricular, intrathecal, intravaginal, transdermal, rectally, by inhalation, or topically to the ears, nose, eyes, or skin. The preferred mode of administration is left to the discretion of the practitioner, and will depend in-part upon the site of the medical condition (such as the site of cancer, a cancerous tumor or a pre-cancerous condition).

In one embodiment, the compounds of the invention are administered parenterally. In a specific embodiment, the compounds of the invention are administered intravenously.

In specific embodiments, it can be desirable to administer one or more compounds of the invention locally to the area in need of treatment (e.g., location of the tumor or ischemic condition). This can be achieved, for example, and not by way of limitation, by local infusion during surgery; topical application, e.g., in conjunction with a wound dressing after surgery; by injection; by means of a catheter; by means of a suppository; or by means of an implant, the implant being of a porous, non-porous, or gelatinous material, including membranes, such as sialastic membranes, or fibers.

In one embodiment, administration can be by direct injection at the site (or former site) of a cancer, tumor, or precancerous tissue.

Pulmonary administration can also be employed, e.g., by use of an inhaler or nebulizer, and formulation with an aerosolizing agent, or via perfusion in a fluorocarbon or synthetic pulmonary surfactant. In certain embodiments, the compounds of the invention can be formulated as a suppository, with traditional binders and carriers such as triglycerides.

In yet another embodiment, the compounds of the invention can be delivered in a controlled release system. In one embodiment, a pump can be used (see Sefton, *CRC Crit. Ref. Biomed. Eng.* 1987, 14, 201; Buchwald et al., Surgery 1980, 88: 507; Saudek et al., *N. Engl. J. Med.* 1989, 321: 574). In another embodiment, polymeric materials can be used (see *Medical Applications of Controlled Release*, Langer and Wise (eds.), CRC Pres., Boca Raton, Fla., 1974; *Controlled Drug Bioavailability, Drug Product Design and Performance*, Smolen and Ball (eds.), Wiley, New York, 1984; Ranger and Peppas, *J. Macromol. Sci. Rev. Macromol. Chem.* 1983, 23, 61; see also Levy et al., *Science* 1985, 228, 190; During et al., *Ann. Neurol.*, 1989, 25, 351; Howard et al., *J. Neurosurg.*, 1989, 71, 105). In yet another embodiment, a controlled-release system can be placed in proximity of the target of the compounds of the invention, e.g., the brain, thus requiring only a fraction of the systemic dose (see, e.g., Goodson, in *Medical Applications of Controlled Release*, supra, vol. 2, 1984, pp. 115-138). Other controlled-release systems discussed in the review by Langer (*Science* 1990, 249, 1527-1533) can be used.

In another embodiment, polymeric materials can be used to achieve controlled or sustained release of the compounds of the invention (see, e.g., U.S. Pat. Nos. 5,679,377; 5,916,597; 5,912,015; 5,989,463; 5,128,326; PCT Publication No. WO 99/15154; and PCT Publication No. WO 99/20253. Examples of polymers used in sustained release formulations include, but are not limited to, poly(2-hydroxy ethyl methacrylate), poly(methyl methacrylate), poly(acrylic acid), poly(ethylene-co-vinyl acetate), poly(methacrylic acid), polyglycolides (PLG), polyanhydrides, poly(N-vinyl pyrrolidone), poly(vinyl alcohol), polyacrylamide, poly(ethylene glycol), polylactides (PLA), poly(lactide-co-glycolides) (PLGA), and polyorthoesters. In a preferred embodiment, the polymer used in a sustained release formulation is inert, free of leachable impurities, stable on storage, sterile, and biodegradable.

Whether in solid, liquid or gaseous form, the compositions of the present invention can comprise an additional active agent selected from among those including, but not limited to, an additional prophylactic agent, an additional therapeutic agent, an antiemetic agent, a hematopoietic colony stimulating factor, an adjuvant therapy, a vaccine or other immune stimulating agent, an antibody/antibody fragment-based agent, an anti-depressant and an analgesic agent. For instance in a particular embodiment, the pharmaceutical composition comprises a compound of the invention, an additional anticancer agent, and a pharmaceutically acceptable carrier or vehicle.

C. Administration of Modulators of Stat Activity

Hyperproliferative disorders, including, but not limited to cancer, neoplasms, tumors, metastases, or any disease or disorder characterized by uncontrolled cell growth as known in the art and described herein, can be treated, suppressed, delayed, managed, inhibited or prevented by administering to a subject in need thereof a prophylactically effective regimen or a therapeutically effective regimen, the regimen comprising administering to the patient a compound of the invention. The invention as it applies to cancer encompasses the treatment, suppression, delaying, management, inhibiting of growth and/or progression, and prevention of cancer or neoplastic disease as described herein.

In one embodiment, the compounds of the invention are administered as monotherapy for the prevention, treatment, and/or management of cancer.

One aspect of the invention relates to a method of preventing, treating, and/or managing cancer in a patient (e.g., a human patient), the method comprising administering to the patient a prophylactically effective regimen or a therapeutically effective regimen, the regimen comprising administering to the patient a compound of the invention or a composition of the invention, wherein the patient has been diagnosed with cancer. The amount of a compound of the invention used in the prophylactic and/or therapeutic regimens which will be effective in the prevention, treatment, and/or management of cancer can be based on the currently prescribed dosage of the compound as well as assessed by methods disclosed herein In one embodiment, the cancer is a hematologic cancer. For instance, the cancer can be leukemia, lymphoma or myeloma. In another embodiment, the cancer is a solid tumor.

In one embodiment of this aspect, the patient has received or is receiving another therapy. In another embodiment of this aspect, the patient has not previously received a therapy for the prevention, treatment, and/or management of the cancer.

The medical practitioner can diagnose the patient using any of the conventional cancer screening methods including, but not limited to physical examination (e.g., prostate examination, breast examination, lymph nodes examination, abdominal examination, skin surveillance), visual methods (e.g., colonoscopy, bronchoscopy, endoscopy), PAP smear analyses (cervical cancer), stool guaiac analyses, blood tests (e.g., complete blood count (CBC) test), blood chemistries including liver function tests, prostate specific antigen (PSA) test, carcinoembryonic antigen (CEA) test, cancer antigen (CA)-125 test, alpha-fetoprotein (AFP)), karyotyping analyses, bone marrow analyses (e.g., in cases of hematological malignancies), histology, cytology, a sputum analysis and imaging methods (e.g., computed tomography (CT), magnetic resonance imaging (MRI), ultrasound, X-ray imaging, mammograph imaging, bone scans).

Another aspect of the invention relates to a method of preventing, treating, and/or managing a solid tumor in a patient (e.g., a human patient), the method comprising administering to a patient in need thereof a prophylactically effective regimen or a therapeutically effective regimen, the regimen comprising administering to the patient a compound or composition of the invention wherein the patient has been diagnosed with a solid tumor, and wherein the patient has undergone a primary therapy to reduce the bulk of the tumor. The primary therapy to reduce the tumor bulk size is preferably a therapy other than a compound or composition of the invention. In specific embodiment of this aspect, the solid tumor is fibrosarcoma, myxosarcoma, liposarcoma, chondrosarcoma, osteogenic sarcoma, chordoma, angiosarcoma, endotheliosarcoma, lymphangiosarcoma, lymphangioendotheliosarcoma, synovioma, mesothelioma, Ewing's tumor, leiomyosarcoma, rhabdomyosarcoma, colon cancer, colorectal cancer, kidney cancer, pancreatic cancer, bone cancer, breast cancer, ovarian cancer, prostate cancer, esophageal cancer, stomach cancer, oral cancer, nasal cancer, throat cancer, squamous cell carcinoma, basal cell carcinoma, adenocarcinoma, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilms' tumor, cervical cancer, uterine cancer, testicular cancer, small cell lung carcinoma, bladder carcinoma, lung cancer, epithelial carcinoma, glioma, glioblastoma multiforme, astrocytoma, medulloblastoma, craniopharyngioma, ependymoma, pinealoma, hemangioblastoma, acoustic neuroma, oligodendroglioma, meningioma, skin cancer, melanoma, neuroblastoma, retinoblastoma, embryonal brain tumor, PNET, or choroid plexus tumor.

Another aspect of the invention relates to a method of preventing, treating, and/or managing cancer, the method comprising administering to a patient in need thereof a prophylactically effective regimen or a therapeutically effective regimen, the regimen comprising administering to the patient a compound of the invention (as described above), or a pharmaceutically acceptable salt thereof wherein the patient received another therapy. In some embodiments, the prior therapy is, for example, chemotherapy, radioimmunotherapy, toxin therapy, prodrug-activating enzyme therapy, antibody therapy, surgical therapy, immunotherapy, radiation therapy, targeted therapy or any combination thereof.

In some embodiments, the prior therapy has failed in the patient. In some embodiments, the therapeutically effective regimen comprising administration of a compound of the invention is administered to the patient immediately after patient has undergone the prior therapy. For instance, in certain embodiments, the outcome of the prior therapy may be unknown before the patient is administered a compound of the invention.

Another aspect of the invention relates to a method of preventing, treating, and/or managing a solid tumor in a patient (e.g., a human patient), the method comprising administering to a patient in need thereof a prophylactically effective regimen or a therapeutically effective regimen, the regimen comprising administering to the patient a compound or composition of the invention, wherein the compound or composition of the invention is administered at a dose that is lower than the human equivalent dosage (HED) of the no observed adverse effect level (NOAEL) over a period of three months, four months, six months, nine months, 1 year, 2 years, 3 years, 4 years or more. The NOAEL, as determined in animal studies, is useful in determining the maximum recommended starting dose for human clinical trials. For instance, the NOAELs can be extrapolated to determine human equivalent dosages. Typically, such extrapolations between species are conducted based on the doses that are normalized to body surface area (i.e., $mg/m^2$). In specific embodiments, the NOAELs are determined in mice, hamsters, rats, ferrets, guinea pigs, rabbits, dogs, primates, primates (monkeys, marmosets, squirrel monkeys, baboons), micropigs or minipigs. For a discussion on the use of NOAELs and their extrapolation to determine human equivalent doses, see *Guidance for Industry Estimating the Maximum Safe Starting Dose in Initial Clinical Trials for Therapeutics in Adult Healthy Volunteers*, U.S. Department of Health and Human Services Food and Drug Administration Center for Drug Evaluation and Research (CDER), Pharmacology and Toxicology, July 2005.

In certain embodiments, the regimens comprise administering a prophylactically effective regimen and/or a therapeutically effective regimen, wherein the regimen results in a reduction in the cancer cell population in the patient. In one embodiment, the patient undergoing the regimen is monitored to determine whether the regimen has resulted in a reduction in the cancer cell population in the patient.

Typically, the monitoring of the cancer cell population is conducted by detecting the number or amount of cancer cells in a specimen extracted from the patient. Methods of detecting the number or amount of cancer cells in a specimen are known in the art. This monitoring step is typically performed at least 1, 2, 4, 6, 8, 10, 12, 14, 15, 16, 18, 20, or 30 days after the patient begins receiving the regimen.

In some embodiments, the specimen may be a blood specimen, wherein the number or amount of cancer cells per unit of volume (e.g., 1 mL) or other measured unit (e.g., per unit field in the case of a histological analysis) is quantitated. The cancer cell population, in certain embodiments, can be determined as a percentage of the total blood cells.

In other embodiments, the specimen extracted from the patient is a tissue specimen (e.g., a biopsy extracted from suspected cancerous tissue), where the number or amount of cancer cells can be measured, for example, on the basis of the number or amount of cancer cells per unit weight of the tissue.

The number or amount of cancer cells in the extracted specimen can be compared with the numbers or amounts of cancer cells measured in reference samples to assess the efficacy of the regimen and amelioration of the cancer under therapy. In one embodiment, the reference sample is a specimen extracted from the patient undergoing therapy, wherein the specimen from the patient is extracted at an earlier time point (e.g., prior to receiving the regimen, as a baseline reference sample, or at an earlier time point while receiving the therapy). In another embodiment, the reference sample is extracted from a healthy, noncancer-afflicted patient.

In other embodiments the cancer cell population in the extracted specimen can be compared with a predetermined reference range. In a specific embodiment, the predetermined reference range is based on the number or amount of cancer cells obtained from a population(s) of patients suffering from the same type of cancer as the patient undergoing the therapy.

If the reduction in the cancer cell population is judged too small upon comparing the number, amount, or percentage of cancer cells in the specimen extracted from the patients undergoing therapy with the reference specimen, then the medical practitioner has a number of options to adjust the therapeutic regimen. For instance, the medical practitioner can then either increase the dosage of the compound or composition of the invention administered, the frequency of the administration, the duration of administration, or any combination thereof. In a specific embodiment, after the determination is made, a second effective amount of a compound or composition of the invention can be administered to the patient.

In other embodiments, the regimens comprise administering a compound or composition of the invention, wherein the regimen results in a reduction in the number, amount, or percentage of cancer stem cells and a reduction in the number, amount, or percentage of cancer cells in the patient.

The amount of a compound of the invention used in the prophylactic and/or therapeutic regimens which will be effective in the prevention, treatment, and/or management of cancer can be based on the currently prescribed dosage of the compound as well as assessed by methods disclosed herein and known in the art. The frequency and dosage will vary also according to factors specific for each patient depending on the specific compounds administered, the severity of the cancerous condition, the route of administration, as well as age, body, weight, response, and the past medical history of the patient. For example, the dosage of a compound of the invention which will be effective in the treatment, prevention, and/or management of cancer can be determined by administering the compound to an animal model such as, e.g., the animal models disclosed herein or known to those skilled in the art. In addition, in vitro assays may optionally be employed to help identify optimal dosage ranges.

In some embodiments, the prophylactic and/or therapeutic regimens comprise titrating the dosages administered to the patient so as to achieve a specified measure of therapeutic efficacy. Such measures include a reduction in the cancer cell population in the patient.

In certain embodiments, the dosage of the compound of the invention in the prophylactic and/or therapeutic regimen is adjusted so as to achieve a reduction in the number or amount of cancer cells found in a test specimen extracted from a patient after undergoing the prophylactic and/or therapeutic regimen, as compared with a reference sample. Here, the reference sample is a specimen extracted from the patient undergoing therapy, wherein the specimen is extracted from the patient at an earlier time point. In one embodiment, the reference sample is a specimen extracted from the same patient, prior to receiving the prophylactic and/or therapeutic regimen. In specific embodiments, the number or amount of cancer cells in the test specimen is at least 2%, 5%, 10%, 15%, 20%, 30%, 40%, 50%, 60%, 70%, 80%, 90%, 95% or 99% lower than in the reference sample.

In some embodiments, the dosage of the compound of the invention in the prophylactic and/or therapeutic regimen is adjusted so as to achieve a number or amount of cancer cells that falls within a predetermined reference range. In these embodiments, the number or amount of cancer cells in a test specimen is compared with a predetermined reference range.

In other embodiments, the dosage of the compound of the invention in prophylactic and/or therapeutic regimen is adjusted so as to achieve a reduction in the number or amount of cancer cells found in a test specimen extracted from a patient after undergoing the prophylactic and/or therapeutic regimen, as compared with a reference sample, wherein the reference sample is a specimen is extracted from a healthy, noncancer-afflicted patient. In specific embodiments, the number or amount of cancer cells in the test specimen is at least within 60%, 50%, 40%, 30%, 20%, 15%, 10%, 5%, or 2% of the number or amount of cancer cells in the reference sample.

In treating certain human patients having solid tumors, extracting multiple tissue specimens from a suspected tumor site may prove impracticable. In these embodiments, the dosage of the compounds of the invention in the prophylactic and/or therapeutic regimen for a human patient is extrapolated from doses in animal models that are effective to reduce the cancer population in those animal models. In the animal models, the prophylactic and/or therapeutic regimens are adjusted so as to achieve a reduction in the number or amount of cancer cells found in a test specimen extracted from an animal after undergoing the prophylactic and/or therapeutic regimen, as compared with a reference sample. The reference sample can be a specimen extracted from the same animal, prior to receiving the prophylactic and/or therapeutic regimen. In specific embodiments, the number or amount of cancer cells in the test specimen is at least 2%, 5%, 10%, 15%, 20%, 30%, 40%, 50% or 60% lower than in the reference sample. The doses effective in reducing the number or amount of cancer cells in the animals can be normalized to body surface area (e.g., mg/m$^2$) to provide an equivalent human dose.

The prophylactic and/or therapeutic regimens disclosed herein comprise administration of compounds of the invention or pharmaceutical compositions thereof to the patient in a single dose or in multiple doses (e.g., 1, 2, 3, 4, 5, 6, 7, 8, 10, 15, 20, or more doses).

In one embodiment, the prophylactic and/or therapeutic regimens comprise administration of the compounds of the invention or pharmaceutical compositions thereof in multiple doses. When administered in multiple doses, the compounds or pharmaceutical compositions are administered with a frequency and in an amount sufficient to prevent, treat, and/or manage the condition. In one embodiment, the frequency of administration ranges from once a day up to about once every eight weeks. In another embodiment, the frequency of administration ranges from about once a week up to about once every six weeks. In another embodiment, the frequency of administration ranges from about once every three weeks up to about once every four weeks.

Generally, the dosage of a compound of the invention administered to a subject to prevent, treat, and/or manage cancer is in the range of 0.01 to 500 mg/kg, and more typically, in the range of 0.1 mg/kg to 100 mg/kg, of the subject's body weight. In one embodiment, the dosage administered to a subject is in the range of 0.1 mg/kg to 50 mg/kg, or 1 mg/kg to 50 mg/kg, of the subject's body weight, more preferably in the range of 0.1 mg/kg to 25 mg/kg, or 1 mg/kg to 25 mg/kg, of the patient's body weight.

In a specific embodiment, the dosage of a compound of the invention administered to a subject to prevent, treat, and/or manage cancer in a patient is 500 mg/kg or less, preferably 250 mg/kg or less, 100 mg/kg or less, 95 mg/kg or less, 90 mg/kg or less, 85 mg/kg or less, 80 mg/kg or less, 75 mg/kg or less, 70 mg/kg or less, 65 mg/kg or less, 60 mg/kg or less, 55 mg/kg or less, 50 mg/kg or less, 45 mg/kg or less, 40 mg/kg or less, 35 mg/kg or less, 30 mg/kg or less, 25 mg/kg or less, 20 mg/kg or less, 15 mg/kg or less, 10 mg/kg or less, 5 mg/kg or less, 2.5 mg/kg or less, 2 mg/kg or less, 1.5 mg/kg or less, or 1 mg/kg or less of a patient's body weight.

In another specific embodiment, the dosage of a compound of the invention administered to a subject to prevent, treat, and/or manage cancer in a patient is a unit dose of 0.1 to 50 mg, 0.1 mg to 20 mg, 0.1 mg to 15 mg, 0.1 mg to 12 mg, 0.1 mg to 10 mg, 0.1 mg to 8 mg, 0.1 mg to 7 mg, 0.1 mg to 5 mg, 0.1 to 2.5 mg, 0.25 mg to 20 mg, 0.25 to 15 mg, 0.25 to 12 mg, 0.25 to 10 mg, 0.25 to 8 mg, 0.25 mg to 7 mg, 0.25 mg to 5 mg, 0.5 mg to 2.5 mg, 1 mg to 20 mg, 1 mg to 15 mg, 1 mg to 12 mg, 1 mg to 10 mg, 1 mg to 8 mg, 1 mg to 7 mg, 1 mg to 5 mg, or 1 mg to 2.5 mg.

In a specific embodiment, the dosage of a compound of the invention administered to a subject to prevent, treat, and/or manage cancer in a patient is in the range of 0.01 to 10 g/m$^2$, and more typically, in the range of 0.1 g/m$^2$ to 7.5 g/m$^2$, of the subject's body weight. In one embodiment, the dosage administered to a subject is in the range of 0.5 g/m$^2$ to 5 g/m$^2$, or 1 g/m$^2$ to 5 g/m$^2$ of the subject's body's surface area.

In other embodiments, the prophylactic and/or therapeutic regimen comprises administering to a patient one or more doses of an effective amount of a compound of the invention, wherein the dose of an effective amount achieves a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention.

In other embodiments, the prophylactic and/or therapeutic regimen comprises administering to a patient a plurality of doses of an effective amount of a compound of the invention, wherein the plurality of doses maintains a plasma level of at least 0.1 µg/mL, at least 0.5 µg/mL, at least 1 µg/mL, at least 2 µg/mL, at least 5 µg/mL, at least 6 µg/mL, at least 10 µg/mL, at least 15 µg/mL, at least 20 µg/mL, at least 25 µg/mL, at least 50 µg/mL, at least 100 µg/mL, at least 125 µg/mL, at least 150 µg/mL, at least 175 µg/mL, at least 200 µg/mL, at least 225 µg/mL, at least 250 µg/mL, at least 275 µg/mL, at least 300 µg/mL, at least 325 µg/mL, at least 350 µg/mL, at least 375 µg/mL, or at least 400 µg/mL of the compound of the invention for at least 1 day, 1 month, 2 months, 3 months, 4 months, 5 months, 6 months, 7 months, 8 months, 9 months, 10 months, 11 months, 12 months, 15 months, 18 months, 24 months or 36 months.

In some embodiments, the prophylactic and/or therapeutic regimen comprises administration of a compound of the invention in combination with one or more additional anticancer therapeutics. Preferably, the dosages of the one or more additional anticancer therapeutics used in the combination therapy is lower than those which have been or are currently being used to prevent, treat, and/or manage cancer. The recommended dosages of the one or more additional anticancer therapeutics currently used for the prevention, treatment, and/or management of cancer can be obtained from any reference in the art including, but not limited to, Hardman et al., eds., *Goodman & Gilman's The Pharmacological Basis Of Basis Of Therapeutics*, 10*th ed.*, Mc-Graw-Hill, New York, 2001; *Physician's Desk Reference* (60$^{th}$ ed., 2006), which is incorporated herein by reference in its entirety.

The compound of the invention and the one or more additional anticancer therapeutics can be administered separately, simultaneously, or sequentially. In various embodiments, the compound of the invention and the additional anticancer therapeutic are administered less than 5 minutes apart, less than 30 minutes apart, less than 1 hour apart, at about 1 hour apart, at about 1 to about 2 hours apart, at about 2 hours to about 3 hours apart, at about 3 hours to about 4 hours apart, at about 4 hours to about 5 hours apart, at about 5 hours to about 6 hours apart, at about 6 hours to about 7 hours apart, at about 7 hours to about 8 hours apart, at about 8 hours to about 9 hours apart, at about 9 hours to about 10 hours apart, at about 10 hours to about 11 hours apart, at about 11 hours to about 12 hours apart, at about 12 hours to 18 hours apart, 18 hours to 24 hours apart, 24 hours to 36 hours apart, 36 hours to 48 hours apart, 48 hours to 52 hours apart, 52 hours to 60 hours apart, 60 hours to 72 hours apart, 72 hours to 84 hours apart, 84 hours to 96 hours apart, or 96 hours to 120 hours part. In preferred embodiments, two or more anticancer therapeutics are administered within the same patient visit.

In certain embodiments, the compound of the invention and the additional anticancer therapeutic are cyclically administered. Cycling therapy involves the administration of one anticancer therapeutic for a period of time, followed by the administration of a second anticancer therapeutic for a period of time and repeating this sequential administration, i.e., the cycle, in order to reduce the development of resistance to one or both of the anticancer therapeutics, to avoid or reduce the side effects of one or both of the anticancer therapeutics, and/or to improve the efficacy of the therapies.

In a preferred embodiment, the anticancer therapeutics are administered concurrently to a subject in separate compositions. The combination anticancer therapeutics of the invention may be administered to a subject by the same or different routes of administration.

In a specific embodiment, cycling therapy involves the administration of a first anticancer therapeutic for a period of time, followed by the administration of a second anticancer therapeutic for a period of time, optionally, followed by the administration of a third anticancer therapeutic for a period of time and so forth, and repeating this sequential administration, i.e., the cycle in order to reduce the development of resistance to one of the anticancer therapeutics, to avoid or reduce the side effects of one of the anticancer therapeutics, and/or to improve the efficacy of the anticancer therapeutics.

When a compound of the invention and the additional anticancer therapeutic are administered to a subject concurrently, the term "concurrently" is not limited to the administration of the anticancer therapeutics at exactly the same time, but rather, it is meant that they are administered to a subject in a sequence and within a time interval such that they can act together (e.g., synergistically to provide an increased benefit than if they were administered otherwise). For example, the anticancer therapeutics may be administered at the same time or sequentially in any order at different points in time; however, if not administered at the same time, they should be administered sufficiently close in time so as to provide the desired therapeutic effect, preferably in a synergistic fashion. The combination anticancer therapeutics of the invention can be administered separately, in any appropriate form and by any suitable route. When the components of the combination anticancer therapeutics are not administered in the same pharmaceutical composition, it is understood that they can be administered in any order to a subject in need thereof. For example, a compound of the invention can be administered prior to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks before), concomitantly with, or subsequent to (e.g., 5 minutes, 15 minutes, 30 minutes, 45 minutes, 1 hour, 2 hours, 4 hours, 6 hours, 12 hours, 24 hours, 48 hours, 72 hours, 96 hours, 1 week, 2 weeks, 3 weeks, 4 weeks, 5 weeks, 6 weeks, 8 weeks, or 12 weeks after) the administration of the additional anticancer therapeutic, to a subject in need thereof. In various embodiments, the anticancer therapeutics are administered 1 minute apart, 10 minutes apart, 30 minutes apart, less than 1 hour apart, 1 hour apart, 1 hour to 2 hours apart, 2 hours to 3 hours apart, 3 hours to 4 hours apart, 4 hours to 5 hours apart, 5 hours to 6 hours apart, 6 hours to 7 hours apart, 7 hours to 8 hours apart, 8 hours to 9 hours apart, 9 hours to 10 hours apart, 10 hours to 11 hours apart, 11 hours to 12 hours apart, no more than 24 hours apart or no more than 48 hours apart. In one embodiment, the anticancer therapeutics are administered within the same office visit. In another embodiment, the combination anticancer therapeutics of the invention are administered at 1 minute to 24 hours apart.

D. In Vitro and In Vivo Testing of Stat Modulators for Hyperproliferative Disorders The compounds of the invention may be demonstrated to inhibit tumor cell proliferation, inhibit tumor cell number, cell transformation and tumorigenesis in vitro or in vivo using a variety of assays known in the art, or described herein. Such assays can use cells of a cancer cell line or cells from a patient in the presence and absence of the compound of interest. Preferably the cell has dysregulated Stat (e.g., enhanced Stat3 activation or decreased Stat1 activation). The ability of a compound or a regimen of the invention to reduce the number of cancer cells or inhibit their proliferation can be assessed by: detecting the expression of antigens on, cancer cells; detecting the proliferation of cancer. Techniques known to those of skilled in the art can be used for measuring these activities. For example, cellular proliferation can be assayed by $^3$H-thymidine incorporation assays and trypan blue cell counts. Antigen expression can be assayed, for example, by immunoassays including, but are not limited to, competitive and non-competitive assay systems using techniques such as western blots, immunohistochemistry radioimmunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, flow cytometry and FACS analysis.

A compound, pharmaceutical composition, or regimen of the invention is preferably tested in vitro and then in vivo for the desired therapeutic or prophylactic activity prior to use in humans. For example, assays which can be used to determine whether administration of a specific compound is effective include cell culture assays in which a patient tissue sample (e.g., a cancer stem cell or cancer cell) is grown in culture and exposed to, or otherwise contacted with, a compound of the invention, and the effect of such compound upon the tissue sample is observed. The tissue sample can be obtained by biopsy from the patient. This test allows the identification of the therapeutically most effective therapy (e.g., prophylactic or therapeutic agent) for each individual patient.

Many assays well-known in the art can be used to assess such survival and/or growth, for example, cell proliferation can be assayed by measuring ($^3$H) thymidine incorporation, by direct cell count, by detecting changes in transcription, translation or activity of known genes such as proto-oncogenes (e.g., fos, Myc) or cell cycle markers (Rb, cdc2, cyclin A, cyclin B, D1, D2, or E). The levels of such protein and mRNA and activity can be determined by any method well known in the art. For example, protein can be quantitated by known immunodiagnostic methods such as Western blotting or immunoprecipitation using commercially available antibodies (for example, many cell cycle marker antibodies can be obtained from Santa Cruz, Inc.). mRNA can be quantitated by methods that are well known and routine in the art, for example by Northern analysis, RNase protection, the polymerase chain reaction in conjunction with reverse transcription, etc. Cell viability can be assessed by using trypan-blue staining or other cell death or viability markers known in the art. Differentiation can be assessed visually based on changes in morphology, etc. The present invention provides for cell cycle and cell proliferation analysis by a variety of techniques known in the art, including but not limited to the following those disclosed herein. As one example, bromodeoxyuridine ("BRDU") incorporation may be used as an assay to identify proliferating cells. The BRDU assay identifies a cell population undergoing DNA synthesis by incorporation of BRDU into newly synthesized DNA. Newly synthesized DNA may then be detected using an anti-BRDU antibody (see Hoshino 30 et al., 1986, Int. J. Cancer 38, 369; Carnpana et al., 1988, J. Immunol. Moth. 107, 79).

Cell proliferation may also be examined using ($^3$H)-thymidine incorporation (see, e.g., Chen, J., 1996, Oncogene 13:1395-403; Jeoung, J., 1995, J. Biol. Chem. 270:18367 73). This assay allows for quantitative characterization of S-phase DNA synthesis. In this assay, cells synthesizing DNA will incorporate ($^3$H)-thymidine into newly synthesized DNA. Incorporation may then be measured by standard techniques in the art such as by counting of radioisotope in a Scintillation counter (e.g., Beckman LS 3800 Liquid Scintillation Counter).

Detection of proliferating cell nuclear antigen (PCNA) may also be used to measure cell proliferation. PCNA is a 36 kilodalton protein whose expression is elevated in proliferating cells, particularly in early G1 and S phases of the cell cycle and therefore may serve as a marker for proliferating cells. Positive cells are identified by immunostaining using an anti-PCNA antibody (see Li et al., 1996, Curr. Biol. 6:189-199; Vassilev et al., 10 1995, J. Cell Sci. 108:1205-15).

Cell proliferation may be measured by counting samples of a cell population over time (e.g., daily cell counts). Cells may be counted using a hemacytometer and light microscopy (e.g., HyLite hemacytometer, Hausser Scientific). Cell number may be plotted against time in order to obtain a growth curve for the population of interest. In a preferred embodiment, cells counted by this method are first mixed with the dye Trypan-blue (Sigma), such that living cells exclude the dye, and are counted as viable members of the population. DNA content and/or mitotic index of the cells may be measured, for example, based on the DNA ploidy value of the cell. For example, cells in the G1 phase of the cell cycle generally contain a 2N DNA ploidy value. Cells in which DNA has been replicated but have not progressed through mitosis (e.g., cells in S-phase) will exhibit a ploidy value higher than 2N and up to 4N DNA content. Ploidy value and cell-cycle kinetics may be further measured using propidum iodide assay (see, e.g., Turner, T., et al., 1998, Prostate 34:175-81). Alternatively, the DNA ploidy may be determined by quantitation of DNA Feulgen staining (which binds to DNA in a stoichiometric manner) on a computerized microdensitometry staining system (see, e.g., Bacus, S., 1989, Am. J. Pathol. 135:783-92).

In another embodiment, DNA content may be analyzed by preparation of a chromosomal spread (Zabalou, S., 1994, Hereditas. 120:127-40; Pardue, 1994, Meth. Cell Biol. 44:333 351). The expression of cell-cycle proteins (e.g., CycA. CycB, CycE, CycD, cdc2, Cdk4/6, Rb, p21 or p27) provide crucial information relating to the proliferative state of a cell or population of cells. For example, identification in an anti-proliferation signaling pathway may be indicated by the induction of p21 cip 1. Increased levels of p21 expression in cells results in delayed entry into G1 of the cell cycle (Harper et al., 1993, Cell 75:805 to 816; Li et al., 1996, Curr. Biol. 6:189-199). p21 induction may be identified by immunostaining using a specific anti-p21 antibody available commercially (e.g. from Santa Cruz, Inc.). Similarly, cell-cycle proteins may be examined by Western blot analysis using commercially available antibodies. In another embodiment, cell populations are synchronized prior to detection of a cell cycle protein. Cell-cycle proteins may also be detected by FACS (fluorescence-activated cell sorter) analysis using antibodies against the protein of interest.

Detection of changes in length of the cell cycle or speed of cell cycle may also be used to measure inhibition of cell proliferation by a compound of the invention. In one embodiment the length of the cell cycle is determined by the doubling time of a population of cells (e.g., using cells contacted or not contacted with one or more compounds of the invention). In another embodiment, FACS analysis is used to analyze the phase of cell cycle progression, or purify G1, S, and G2/M fractions (see, e.g., Delia, D. et al., 1997, Oncogene 14:2137-47).

Lapse of cell cycle checkpoint(s), and/or induction of cell cycle checkpoint(s), may be examined by the methods described herein, or by any method known in the art. Without limitation, a cell cycle checkpoint is a mechanism which ensures that a certain cellular events occur in a particular order. Checkpoint genes are defined by mutations that allow late events to occur without prior completion of an early event (Weiner, T., and Hartwell, L., 1993, Genetics, 134:63-80). Induction or inhibition of cell cycle checkpoint genes may be assayed, for example, by Western blot analysis, or by immunostaining, etc. Lapse of cell cycle checkpoints may be further assessed by the progression of a cell through the checkpoint without prior occurrence of specific events (e.g. progression into mitosis without complete replication of the genomic DNA).

Activity of signaling and cell cycle proteins and/or protein complexes is often mediated by a kinase activity. The present invention provides for analysis of kinase activity by assays such as the histone HI assay (see, e.g., Delia, D. et al., 1997, Oncogene 14:2137 47). The compounds of the invention can also be demonstrated to alter cell proliferation in cultured cells in vitro using methods which are well known in the art. Specific examples of cell culture models include, but are not limited to, for lung cancer, primary rat lung tumor cells (Swafford et al., 1997, Mol. Cell. Biol., 17:1366-1374) and large-cell undifferentiated cancer cell lines (Mabry et al., 1991, Cancer Cells, 3:53-58); colorectal cell lines for colon cancer (Park and Gazdar, 1996, J. Cell Biochem. Suppl.

24:131-141); multiple established cell lines for breast cancer (Hambly et al., 1997, Breast Cancer Res. Treat. 43:247-258; Gierthy et al., 1997, Chemosphere 34:1495-1505; Prasad and Church, 1997, Biochem. Biophys. Res. Commun. 232:14-19); a number of well-characterized cell models for prostate cancer (Webber et al., 1996, Prostate, Part 1, 29:386-394; Part 2, 30:58-64; and Part 3, 30:136-142; Boulikas, 1997, Anti-cancer Res. 17:1471-1505); for genitourinary cancers, continuous human bladder cancer cell lines (Ribeiro et al., 1997, Int. J. Radial. Biol. 72:11-20); organ cultures of transitional cell carcinomas (Booth et al., 1997, Lab Invest. 76:843-857) and rat progression models (Vet et al., 1997, Biochim. Biophys Acta 1360:39-44); and established cell lines for leukemias and lymphomas (Drexler, 1994, Leuk. Res. 18:919-927, Tohyama, 1997, Int. J. Hematol. 65:309-317).

The compounds of the invention can also be demonstrated to inhibit cell transformation (or progression to malignant phenotype) in vitro. In this embodiment, cells with a transformed cell phenotype are contacted with one or more compounds of the invention, and examined for change in characteristics associated with a transformed phenotype (a set of in vitro characteristics associated with a tumorigenic ability in vivo), for example, but not limited to, colony formation in soft agar, a more rounded cell morphology, looser substratum attachment, loss of contact inhibition, loss of anchorage dependence, release of proteases such as plasminogen activator, increased sugar transport, decreased serum requirement, or expression of fetal antigens, etc. (see Luria et al., 1978, General 30 Virology, 3-D Ed., John Wiley & Sons, New York, pp. 436-446). Loss of invasiveness or decreased adhesion may also be used to demonstrate the anti-cancer effects of the compounds of the invention. For example, a critical aspect of the formation of a metastatic cancer is the ability of a precancerous or cancerous cell to detach from primary site of disease and establish a novel colony of growth at a secondary site. The ability of a cell to invade peripheral sites is reflective of a potential for a cancerous state.

Loss of invasiveness may be measured by a variety of techniques known in the art including, for example, induction of E-cadherin-mediated cell-cell adhesion. Such E cadherin-mediated adhesion can result in phenotypic reversion and loss of invasiveness (Hordijk et al., 1997, Science 278:1464-66). Loss of invasiveness may further be examined by inhibition of cell migration. A variety of 2-dimensional and 3-dimensional cellular matrices are commercially available (Calbiochem-Novabiochem Corp. San Diego, Calif.). Cell migration across or into a matrix may be examined by microscopy, time-lapsed photography or videography, or by any method in the art allowing measurement of cellular migration. In a related embodiment, loss of invasiveness is examined by response to hepatocyte growth factor (HGF). HGF induced cell scattering is correlated with invasiveness of cells such as Madin-Darby canine kidney (MDCK) cells. This assay identifies a cell population that has lost cell scattering activity in response to HGF (Hordijk et al., 1997, Science 278:1464-66).

Alternatively, loss of invasiveness may be measured by cell migration through a chemotaxis chamber (Neuroprobe/Precision Biochemicals Inc. Vancouver, BC). In such assay, a chemo-attractant agent is incubated on one side of the chamber (e.g., the bottom chamber) and cells are plated on a filter separating the opposite side (e.g., the top chamber). In order for cells to pass from the top chamber to the bottom chamber, the cells must actively migrate through small pores in the filter. Checkerboard analysis of the number of cells that have migrated may then be correlated with invasiveness (see, e.g., Ohnishi, T., 1993, Biochem. Biophys. Res. Commun. 193: 518-25).

The compounds of the invention can also be demonstrated to inhibit tumor formation in vivo. The compounds, pharmaceutical compositions, and regimens of the invention can be tested in suitable animal model systems prior to use in humans. Such animal model systems include, but are not limited to, rats, mice, chicken, cows, monkeys, pigs, dogs, rabbits, etc. Any animal system well-known in the art may be used. Several aspects of the procedure may vary; said aspects include, but are not limited to, the temporal regime of administering the therapeutic modalities (e.g., prophylactic and/or therapeutic agents), whether such therapeutic modalities are administered separately or as an admixture, and the frequency of administration of the therapeutic modalities.

A vast number of animal models of hyperproliferative disorders, including tumorigenesis and metastatic spread, are known in the art and are disclosed herein (see Chapter 317, "Principals of Neoplasia," in Harrison's: Principals of Internal Medicine, 13th Edition, Isselbacher et al., eds., McGraw-Hill, New York, p. 1814, and Lovejoy et al., 1997, J. Pathol. 181:130-135). Specific examples include for lung cancer, transplantation of tumor nodules into rats (Wang et al., 1997, Ann. Thorac. Surg. 64:216-219) or establishment of lung cancer metastases in SCID mice depleted of NK cells (Yono and Sone, 1997, Gan To Kagaku Ryoho 24:489-494); for colon cancer, colon cancer transplantation of human colon cancer cells into nude mice (Gutman and Fidler, 1995, World J. Surg. 19:226-234), the cotton top tamarin model of human ulcerative colitis (Warren, 1996, Aliment. Pharmacol. Ther. Supp 12:45-47) and mouse models with mutations of the adenomatous polyposis tumor suppressor (Polakis, 1997, Biochim. Biophys. Acta 1332:F127-F147); for breast cancer, kansgenic models of breast cancer (Dankort and Muller, 1996, Cancer Treat. Res. 83:71-88; Amundadittir et al., 1996, Breast Cancer Res. Treat. 39:119-135) and chemical induction of tumors in rats (Russo and Russo, 5 1996, Breast Cancer Res. Treat. 39:7-20); for prostate cancer, chemically-induced and transgenic rodent models, and human xenograft models (Royal et al., 1996, Semin. Oncol. 23:35-40), for genitourinary cancers, induced bladder neoplasm in rats and mice (Oyasu, 1995, Food Chem. Toxicol 33:747-755) and xenografts of human transitional cell carcinomas into nude rats (Jarrett et al., 1995, J. Endourol. 9:1-7); and for hematopoietic cancers, transplanted allogeneic marrow in animals (Appelbaum, 1997, Leukemia 11 (Suppl. 4):S15-S17). Further, general animal models applicable to many types of cancer have been described, including, but not restricted to, the p53-deficient mouse model (Donehower, 1996, Semin. Cancer Biol. 7:269-278), the Min mouse (Shoemaker et al., 1997, Biochem. Biophys. Acta, 1332:F25-F48), and immune responses to tumors in rat 15 (Frey, 1997, Methods, 12:173-188).

For example, a compound of the invention can be administered to a test animal, in one embodiment a test animal predisposed to develop a type of tumor, and the test animal subsequently examined for a decreased incidence of tumor formation in comparison with an animal not administered the compound. Alternatively, a compound can be administered to test animals having tumors (e.g., animals in which tumors have been induced by introduction of malignant, neoplastic, or transformed cells, or by administration of a carcinogen) and subsequently examining the tumors in the test animals for tumor regression in comparison to animals not administered the compound. A compound of the invention is considered effective in treating a hyperproliferative disorder when administration of a therapeutically effective amount increases time to tumor progression or increases survival time by at least 5%, preferably at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Similarly, a compound of the invention is considered effective in treating a hyperproliferative disorder when administration of a therapeutically effective amount decreases the rate of tumor growth, decreases tumor mass, decreases the number of metastases by at least 10%, at least 15%, at least 20%, at least 25%, at least 30%, at least 35%, at least 40%, at least 45%, at least 50%, at least 55%, at least 60%, at least 65%, at least 70%, at least 75%, at least 80%, at least 85%, at least 90%, at least 95%, or at least 100%. Such results can be determined by one having ordinary skill in the relevant art, e.g., oncologist.

Further, any assays known to those skilled in the art can be used to evaluate the prophylactic and/or therapeutic utility of a compound or pharmaceutical composition disclosed herein for cancer or one or more symptoms thereof.

V. Stat Modulators for the Treatment or Prevention of Ischemic Disorders

In one embodiment of the invention, methods are provided for treating ischemic disease using a compound of the invention that acts as Stat3 agonists or activators. Suitable compounds of the invention for use in treating ischemic disease includes: mebendazole, nocodazole, nortriptyline hydrochloride, zimelidine dihydrochloride monohydrate, adenosine 5'-monophosphate monohydrate, promazine hydrochloride, podophyllotoxin, ribavirin, deptropine citrate, or 4-(3,4-Dimethyl-phenoxy)-N-hydroxy-benzamidine and detecting Stat3 activity in the cell. Stat3 agonists may be administered to patients in need of such treatment to increase stimulated vessel growth, and consequentially increase tissue perfusion and blood flow, thereby overcoming the vascular insufficiency characteristic of ischemic diseases.

The present compounds are all readily available in the art. Mebendazole is sold under the brand names Ovex, Vermox, Antiox and Pripsen and prescribed for the treatment of pinworms, roundworms and hookworms. Nocodazole is an antineoplastic agent which exerts its effect in cells by depolymerizing microtubules. Nortriptyline hydrochloride is sold under the brand name Aventyl and Pamelor and is used for the treatment of depression and nocturnal enuresis. Zimelidine dihydrochloride monohydrate is sold under the brand name Normud and Zelmid for the treatment of depression. Promazine hydrochloride is prescribed for treating agitation and restlessness. Podophyllotoxin is a topical cream that is prescribed for the treatment of viral warts. Ribavirin is sold under the brand names Copegus' Rebetol, Ribasphere, Vilona and Virazole and used orally or in aerosol form as an anti-viral. Deptropine citrate is an antihistamine for the treatment of respiratory-tract disorders.

The present invention provides methods for preconditioning cells, tissue or organs in order to prevent injury due to ischemia or ischemia/reperfusion. According to the method, the cells, tissues or organs which will undergo or are at risk of undergoing ischemia/reperfusion are exposed to a compound of the invention prior to (and/or during and after) subjection to ischemia/reperfusion. It is believed that such exposure to a compound of the invention prevents or limits damage that would otherwise occur.

By "ischemia" we mean a condition where the blood flow to a tissue or organ is stopped or reduced below a threshold necessary to maintain the viability of the tissue or organ. The stoppage or reduction in blood flow may result from a blockage in the blood vessel supplying the tissue or organ (e.g. during a stroke, or deliberately during surgical procedures), may result when the heart stops beating (e.g. a heart attack), during respiratory disease, in severe anemia and even drowning. Reperfusion is the term which describes the restarting of the supply of blood to the organ or tissue following ischemia. By "preconditioning" we mean the protection of the heart muscle from serious damage in the future by subjecting it to very brief periods of deprivation of blood flow and, therefore, oxygen. Damage to myocardial tissue from ischemia, decreased oxygenated blood flow to muscle tissue, can be reduced by preconditioning. Ischemic preconditioning (PC) was first described by Jennings and colleagues (Murry et al., 1986). Brief periods (5-10 minutes) of ischemia have been shown to precondition against more prolonged periods of ischemia. Such preconditioning appears to provide protection against greater pathologic effects on myocardial tissue that arise from ischemia compared with tissues not preconditioned.

Those of skill in the art will recognize that the compounds mebendazole, nocodazole, nortriptyline hydrochloride, zimelidine dihydrochloride monohydrate, adenosine 5'-monophosphate monohydrate, promazine hydrochloride, podophyllotoxin, ribavirin, deptropine citrate, and 4-(3,4-Dimethyl-phenoxy)-N-hydroxy-benzamidine are activators of Stat3.

Those of skill in the art will recognize that many situations exist in which an individual may be at risk for incurring injury due to ischemia/reperfusion. Examples include but are not limited to when an individual undergoes a surgical procedure such as coronary bypass, coronary arteriography, or angioplasty. During such procedures, the heart is subjected to ischemia and reperfusion and, in the absence of preconditioning, is susceptible to injury. According to the methods of the present invention, a Stat3 activator may be administered to the patient prior to, during, or after such procedure, or at any combination of those times (e.g. before, during and after), in order to prevent or lessen the extent of injury due to ischemia/reperfusion.

Administration of Stat3 activators may serve as an adjunct therapy in, for example, coronary bypass surgery and angioplasty. Examples of other areas in which an individual may be at risk for incurring injury due to ischemia/reperfusion include but are not limited to brain, liver, kidney and other organs.

Further examples of the use of Stat3 activators according to the present invention include the prophylactic use of Stat3 activators in persons who are at risk for developing ischemia-related conditions. Preferred ischemic (or potentially ischemic) tissues that may be treated in accordance with the methods of the present invention include but are not limited to brain, cardiac, liver, kidney, lung, gut, skeletal muscle, spleen, pancreas, nerve, spinal cord, retinal tissue, vasculature, and intestinal tissue. An especially preferred tissue is cardiac tissue. Examples of individuals who might benefit from prophylactic treatment with Stat3 activators of the present invention include but are not limited to persons with risk factors for the development of such pathological conditions, e.g. those with risk factors such as: a positive family history of ischemic heart disease, a genetic predisposition to develop ischemic heart disease, diabetes, hyperlipidemia, hypertension, obesity, cigarette smoking, sedentary lifestyle, psychosocial tension and certain personality traits (e.g. "type A personality"). Prophylactic administration of a Stat3 activator results in preconditioning of the cells, tissues and organs exposed thereto and prevents, slows or lessens the extent of the development of ischemic injury.

Those of skill in the art will recognize that, in some cases, ischemic/reperfusion injury may be completely prevented by the administration of Stat3 activators. However, it is also possible that an individual may obtain great benefit even if complete prevention is not attained, e.g. any lessening or slowing of injury due to ischemia/reperfusion, in comparison to injury sustained without a compound of the invention, may be of benefit.

The Stat3 activators used in the practice of the present invention may be administered as a pharmaceutical preparation comprising a pharmaceutically acceptable carrier.

Those of skill in the art will recognize that the exact dosage of the Stat3 activators to be administered may vary depending on factors such as the age, gender, weight and overall health status of the individual patient, as well as on the precise nature of the condition being treated, and on the exact inhibitor being administered. Similarly, the length of duration of treatment with Stat3 activators will vary from individual to individual, and will depend on the application and the inhibitor. For example, for prophylaxis against a genetic predisposition, a relatively low dose may be administered over a period of many months or even years in order to maintain protection. However, in order to achieve protection for a specific event such as heart surgery, relatively higher doses may be administered just prior to (e.g. within hours or a few days) and may cease shortly after completion of the surgical procedure (e.g. within hours or a few days). Preferably, the administered dose of the Stat3 activator is the same as currently prescribed in the art for non-ischemic disorders. In all cases, the amount of Stat3 activators to be administered and the precise treatment protocol is determined by a skilled practitioner such as a physician.

The Stat3 activator may be administered by any of a wide variety of means which are well known to those of skill in the art, (including but not limited to intravenously, intracoronary, intramuscularly, intraperitoneally, orally, rectally, intraocularly, and the like) or by other routes (e.g. transdermal, sublingual, aerosol, etc.) and may be in any form (e.g. liquid, solid, etc.) which is suitable for the particular means of administration. Preferably, the route of administration is the same as currently prescribed for the compound.

Further, the Stat3 activator may be administered either alone or together with other medications in a treatment protocol. For example, a Stat3 activator may be administered either separately or in combination with other cardiac drugs such as beta-adrenergic blockers, calcium channel antagonists and/or aspirin; antioxidants; and either separately or in combination with fibrinolytic drugs such as tissue plasminogen activator (tPA), streptokinase and urokinase; or either alone or in combination with other Stat3 activators.

Those of skill in the art will recognize that many other applications of the method of the present application also exist. For example, the ischemia/reperfusion event need not be of surgical origin but may occur for any of a variety of other reasons. For example, the administration of Stat3 activators may be beneficial for individuals who are suspected of undergoing or have recently (e.g within about 24 hours or less) undergone a heart attack. In this case, administration of the Stat3 activator should occur as soon as possible after the condition is recognized. Nevertheless, if administration cannot or does not occur during or soon after a heart attack (e.g. within 24 hours or less), the administration of the Stat3 activator may still be advantageous due to the delayed cardioprotective effects that Stat3 activators have been shown to exhibit, as demonstrated herein. For example, administration of a Stat3 activator may be beneficial for up to about 24 hours or 7 days after the attack. Examples of other applications include but are not limited to treatment of angina pectoris, unstable angina pectoris, angina pectoris after myocardial infarction, myocardial infarction, acute myocardial infarction and coronary restenosis after percutaneous transluminal coronary angioplasty (PTCA), etc.

In one embodiment of the invention, the cells, tissues or organs that are preconditioned and protected from ischemic/reperfusion injury are cardiac in nature. However, those of skill in the art will recognize that many other types of cells, tissues and organs are susceptible to injury due to ischemic/reperfusion and may be protected by the method of the present invention. Examples of other cell/tissue/organ types include but are not limited to brain, liver, kidney, lung, intestine, nerve, spinal cord, gut, skeletal muscle, spleen, pancreas, spinal cord, retinal tissue and vasculature.

In some applications of the methods of the present invention, the cells, tissues or organs that are treated with a Stat3 activator are located within an individual such as a human patient. However, those of skill in the art will recognize that this need not be the case. For example, it may sometimes be of benefit to treat cells, tissues or organs that have been removed from a donor organism, such as a human or other mammal. The cells, tissues or organs may have been removed or partially removed for any of a variety of reasons, e.g. for a surgical procedure in which they are temporarily completely or partially removed from a patient in order to facilitate the procedure, and then replaced. Alternatively, the cells, tissues or organs may be permanently removed from a donor and used, for example, for the purpose of transplantation to a transplant recipient, or for experimental purposes. Use of the method of the present invention for such purposes will help to maintain viability of transplanted material during transport to the transplant recipient, or of experimental material during experimental procedures. Examples of cells, tissues or organs which can be advantageously treated in this manner include but are not limited to heart, brain liver, kidney, lung, skeletal muscle, spleen, pancreas, retinal tissue and vasculature.

Those of skill in the art will recognize that serious injury due to ischemia or ischemia/reperfusion can occur to both the donor and the recipient during an organ transplant procedure. Thus, prevention and treatment of such injury according to the methods of the present invention may be carried out by administering a Stat3 activator by any of a variety of different strategies. For example, the inhibitor may be administered: to a transplant donor prior to, during or after removal of the organ/tissue that is being donated; to a transplant recipient prior to, during or after receipt of the organ/tissue that is being donated; or directly to the organ/tissue itself either prior to removal from the donor, after transplantation into the recipient, or during the time after removal and before transplant, e.g. during storage and transportation of the organ/tissue.

While in some embodiments, the cells, tissues or organs that are treated by the methods of the present invention are human in origin, this need not be the case. Those of skill in the art will recognize that the cells, tissues or organs of other mammals may also benefit from the methods of the present invention. Thus, veterinarian and cross-species transplant applications are also contemplated. Further, individuals treated with Stat3 activators according to the methods of the present invention may be in any stage of life, e.g. new-born, adult, or aging.

In yet another aspect of the present invention, the treatment or prevention of ischemic/reperfusion injury during certain interventional procedures is contemplated. In one embodiment, the interventional procedure is that of removal of a clot, for example, by dissolution with drugs. Those of skill in the art will recognize that much of the damage and risk associated with clot dissolution is associated with the influx of blood into the area that was blocked by the clot and thus subjected to ischemia. Tissues or cells subjected to ischemia undergo changes that make them particularly vulnerable to injury by, for example, inflammatory cells in the blood that is reintroduced. Thus, one aspect of the present invention is to treat or prevent injury associated with ischemia/reperfusion that occurs as a result of clot removal. The treatment involves administration of a Stat3 activator in a quantity sufficient to prevent or lessen damage to cells, tissues, or organs that are affected by the presence and subsequent removal of the clot.

VI. Differentiation Inhibiting Agents for Stem Cells

In another aspect of the invention, the invention is directed to a method for maintaining a stem cell in an undifferentiated state. The method includes contacting the stem cell with a pharmacologically effective dose of a stem cell differentiation inhibiting agent according to the present invention. Differentiation inhibiting agents according to the invention include the following Stat3 activators: mebendazole, nocodazole, nortriptyline hydrochloride, zimelidine dihydrochloride monohydrate, adenosine 5'-monophosphate monohydrate, promazine hydrochloride, podophyllotoxin, ribavirin, or 4-(3,4-Dimethyl-phenoxy)-N-hydroxy-benzamidine. It is contemplated that other Stat3 activators are useful in maintaining a stem cell in an undifferentiated state.

The stem cell differentiation inhibiting agents according to the present invention, can be used by adding to a basic culture medium for mammal stem cell culture, which is a basic medium for animal cell culture. Examples of the basic stem cell media for animal cell culture include Dulbecco's modified Eagle medium (DMEM), knockout DMEM, Glasgow MEM (GMEM), RPMI1640 and IMDM (these are Invitrogen Corp., USA made), but are not restricted to these examples. One embodiment of the cell culture medium is Dulbecco's modified Eagle medium (DMEM). In addition, these basic media can be used by adding with proteins involving in cell proliferation and differentiation regulation such as serum or a serum alternate, various kinds of growth factors and cytokines. Further, any compound may be added. Serum may be any serum or serum-based solution to supply a nutrient effective for proliferation and maintaining survival of the stem cell and the embryonic stem cell. Examples of such serum include fetal calf serum (FCS), calf serum (CS), and horse serum (HS). The usable serum replacements include those known to those skilled in the art, proteins, amino acids, lipids, vitamins, and the like independently or in combination of them. Proteins include insulin, transferrin, albumin, peptone, FGF (Fibroblast Growth Factor), EGF (Epithelial Growth Factor) and the like, amino acids include arginine, cysteine, glutamine, glycine, histidine, isoleucine, leucine, lysine, methionine, phenylalanine, serine, threonine, tryptophane, tyrosine, valine and the like, and vitamins include pantothenic acid, choline, folic acid, inositol, nicotinic acid amide, riboflavin, thiamine, pyridoxine and the like, however, restriction is not applied to these compounds. In one embodiment, serum is bovine fetus serum. In more specific embodiment, bovine fetus serum is provided with a concentration between about 25% and about 1%. In more specific embodiment, the concentration of bovine fetus serum in the cell culture medium is 15%. In another embodiment, the serum replacement is knockout serum replacement: KSR (Invitrogen Corp. USA made). The cell growth factors which can be added include a hepatocyte growth factor (HGF), epidermal growth factor (EGF), fibroblast growth factor (FGF), insulin-like growth factor (IGF), nerve growth factor (NGF), platelet-derived growth factor (PDGF), vascular endothelial growth factor (VEGF), transforming growth factor (TGF), bone morphogenetic protein (BMP), stem cell factor (SCF), Wnt, and the like, however, restriction is not applied to these compounds. The cytokines which can be added include interleukin (IL), granulocyte-macrophage colony stimulating factor (GM-CSF), and the like, however, restriction is not applied to these compounds.

Cell culture medium also contains an antioxidant (a reductant) (for instance, .beta.-mercaptoethanol). In a preferable embodiment, β-mercaptoethanol has a concentration of about 0.1 mM. Other antioxidants (for instance, monothioglycerol or dithiothreitol (DTT) independently or in combination) can be used to provide a same effect. Further, other equivalent substances are known to those skilled in the art of cell culture.

The differentiation inhibiting agent according to the present invention and the active ingredient thereof can be used by accompanying any culture medium material or by immobilizing it to the culture medium material. For the culture medium material, a porous material can be used. The porous material is the material having many fine pores and is not specially restricted in a kind, thickness, shape, and size of the material. The kind of the material may be an organic material, an inorganic material, and a complex material composed of an organic material and an inorganic material. The shape of the porous material may be any forms including flat plate, globular, rod-like, fibrous and hollow, and, for example, includes a film, sheet, membrane, board, unwoven fabric, filter paper, sponge, cloth, knitted fabric, lump, thread, hollow tube and particle. For culturing cells, the unwoven fabric is more preferable in consideration of an easily regulatable pore size to support cells for allowing 3-dimensional culture and easy and low cost preparation of the material. The pore size of the porous material is not specially restricted, however, in consideration of 3-dimensional support of cells, an average pore size is preferably between 0.1 µm and 100 µm and further preferably between 1 µm and 50 µm. A fiber diameter is not specially restricted, however, 0.03 denier or smaller is preferable.

In order to increase adhering performance, undifferentiation-maintaining ability, and proliferation ability of cells, the porous material as described above may be subjected to surface coating treatment with a high polymer. The high polymer is the substance that is constructed by linking linearly, squarely, or cubically 1 or more species of monomers being repeating constitutional units and that has a some-hundred molecular weight. The high polymer is classified into 3 major categories: natural high polymer, semisynthesized high polymer, and synthesized high polymer. For the present invention, any high polymers can be used.

For example, the natural high polymer includes mica, asbestos, graphite, diamond, starch, cellulose, saccharides such as alginic acid, and proteins such as gelatin, fibronectin, fibrinogen, laminin, and collagen. The semisynthesized high polymer includes glass, cellulose nitrate, cellulose acetate, rubber hydrochloride, and carboxymethyl cellulose. The synthesized high polymer includes polyphosphonitrile chloride, polyethylene, polyvinyl chloride, polyamide, polyethylene terephthalate, polysulfon, polyacrylonitrile, polyvinyl alcohol, polymethyl methacrylate, polyhydroxyethyl methacrylate, polydimethylaminoethyl methacrylate, and a copolymer, which is composed of 2 or more types of synthesized monomers, represented by the copolymer prepared by hydroxyethyl methacrylate and dimethylaminoethyl methacrylate.

In consideration of easy coating processing, organic high polymers are preferable, and proteins, peptides and synthesized organic high polymers are more preferable. In one embodiment, the culture medium material is gelatin. In another embodiment, Matrigel (BD Bioscience Corp. made.) is used.

Cells cultured by using the differentiation inhibiting agent according to the present invention includes all the stem cells or the embryonic stem cells which can be obtained by using the publicly known methods and materials. The stem cells include, as an example, the stem cell available by the following publicly known method. A marrow cell ("Marrow Transplantation Guide" by H. J. Deeg, H. G Klingemann, G L. Phillips, translated in Japanese by Sinpei Kasakura), a marrow stem cell (Osawa et al., Science 273: p 242-245, 1996, Goodell et al., J. E. Med. 183: p 1797-1806, 1996, Verfaillie et al., Nature 418: p 41, 2002), a neural stem cell (Reynolds et al., Science, p 1707-1710, 1992), a tissue stem cell (Goodell et al., J. E. Med. 183: p 1797-1806, 1996, Matsuzaki et al., Experimental Medicine 19: p 345-349, 2001, Blau et al., Cell, 105: p 829-841, 2001), a mesenchymal stem cell (Liechty et al., Nature Medicine, 6: p 1282-1286, 2000, Pittenger et al., Science 284: p 143-147, 1999) and a skin stem cell and epidermal stem cell (Murota Seiitsu (ed.), "Regeneration Medicine and Regeneration Therapy," Gendai Kagaku Extra Number 41, Tokyo Kagaku Douzin).

The embryonic stem cells to be cultured can be obtained by using the following publicly known method and material. Murine embryonic stem cell: Evans et al., Nature 292: p 154, 1981, bovine ES cell: Schellander et al., Theriogenology 31: p 15-17, 1989, swine ES cell: Strojek et al., Theriogenology 33: p 901, 1990, sheep ES cell: Handyside, Roux's Arch. Dev. Biol. 196: p 185, 1987, hamster ES cell: Doetschman et al., Dev. Biol. 127: p 224, 1988, rhesus monkey ES cell: Thomson et al., Proc. Natl. Acad. Sci. USA 92: p 7844, 1995, cynomolgus monkey ES cell: Suemori et al., Dev. Dyn. 222: p 273, 2001, human ES cell: Thomson et al., Science 282: p 1145, 1998, Reubinoff et al., Nature Biotech 18: p 399, 2000, human EG cell: Gearhart et al., Proc. Natl. Acad. Sci. USA, 95: p 13726, 1998. On the other hand, mouse embryonic stem cell (129SV and C57/BL6) can be obtained from Dai Nippon Seiyaku k.k.

The differentiation inhibiting agent provided according to the present invention can be used for all the stem cells and the embryonic stem cells, and is desirably used for the stem cells and the embryonic stem cells of mammals and more preferably used for the stem cells and the embryonic stem cells of primates.

Cells and embryonic stem cells, which have been once isolated, can be cultured in the undifferentiated state by using the differentiation inhibiting agent of the present invention. The degree of the undifferentiated state of the stem cell, preferably the embryonic stem cell, cultured by using the differentiation inhibiting agent of the present invention can be confirmed by measuring an alkaline phosphatase (ALP) activity existing on a cell membrane of the stem cell. It is known that in an undifferentiated embryonic stem cell, the ALP activity is kept and, when the cell is differentiated, decreases (Williams et al., Nature 336: p 684, 1988, Thomson et al., Science 282: p 1145, 1998). The alkaline phosphatase (ALP) activity is detected by methods including a staining method by using an insoluble substrate or a spectrophotometric method by using a water-soluble substrate. The identification of stem cells by ALP activity is well known in the art (Shamblott, et al., Proc. Natl. Acad. Sci. USA 95; pp. 13726-13731 (1998)) and can be determined with commercial kits such as the ELF Phosphatase Detection Kit for Embryonic Stem Cells (ATCC, Manassas, Va.).

ALP activity can be detected by ALP staining method. A reaction solution containing a phosphate ester salt and a diazonium salt as the substrate are added to cells on a culture dish. The phosphate ester salt is hydrolyzed by alkaline phosphatase present on the cell membrane and, subsequently, a coupling reaction with the diazonium salt produces an azo pigment resulting in sedimentation of the pigment in an ALP active site. Counting number of stained colonies enables quantification of the ALP activity of the cell to allow quantifying the degree of undifferentiation of the cell. ALP staining of the embryonic stem cell cultured by using the differentiation inhibiting agent of the present invention shows that this cell has significantly higher ALP activity than that of a control cell cultured by using a culture medium lacking the differentiation inhibiting agent. This means that the differentiation inhibiting agent of the present invention allows the cell to proliferate while keeping the undifferentiated state of the embryonic stem cell.

In addition, the degree of undifferentiation of the embryonic stem cell can be known by measuring the expression level of the Oct-3/4 gene. The Oct-3/4 gene is a transcription factor belonging to a POU family, and is expressed specifically in the undifferentiated state in the embryonic stem cell and an embryonic cancer cell (EC cell) (Okamoto et al., Cell 60: p 461, 1990) and is expressed only in an undifferentiated cell line (Scholer, Trends Genet 7: p 323, 1991). In addition, homozygous mice of which Oct-3/4 gene has been disrupted, stops development at the blastodermic vesicle stage. Hence, it was found that the Oct-3/4 gene has an important function for keeping the undifferentiated state (Nichols et al., Cell 95: p 379, 1998). On the other hand, it was recently found that an over expression of the Oct-3/4 gene promotes differentiation of the embryonic stem cell (Niwa et al., Nat. Genet. 24: p 372, 2000). Therefore, it is important to keep the expression level of the Oct-3/4 in a specific range to maintain the undifferentiated state. As an embodiment of measuring the expression level of the Oct-3/4 gene, a quantitative PCR (polymerase chain reaction) method can be used.

In one embodiment, a real time PCR method is used to enable a convenient and reliable quantitative measurement having a wide dynamic range. The real time PCR technique includes the method by using a TaqMan probe using ABI-PRISM7700. (Applied Biosystems) and the method by using LightCycler (Roche Diagnostics). Particularly in the latter case, in a high rate reaction cycle in which a temperature cycle of PCR is completed for some 10 minutes, a change of an amplified amount of a DNA synthesized for every cycle can be detected in a real time. DNA detection method of the real time PCR method includes 4 methods using a DNA-binding pigment (intercalator), a hybridization probe (kissing probe), TaqMan probe, or Sunrise Uniprimer (molecular beacon). On the other hand, the expression level of the Oct-3/4 gene can be analyzed by using a DNA-binding pigment such as SYBR GreenI. SYBR GreenI is a binding pigment specific to a double strand of the DNA and, when bound to a double strand, an inherent fluorescence intensity is reinforced. By adding SYBR GreenI at the PCR reaction and measuring the fluorescence intensity at the end of each cycle of an elongation reaction, the increase in a PCR product can be detected. For detection of Oct-3/4 gene, similar to normal PCR, a primer is designed by using a commercialized gene analysis software on the basis of a sequence of the Oct-3/4 gene. SYBR GreenI detects a nonspecific product and, thus, requires designing an optimal primer. Required designing standards are a length of an oligomer, a base composition of the sequence, a GC content, and a Tm value.

Frequently, quantitative PCR aims to know the amount of a target DNA for a specific amount of a sample. For this purpose, an evaluation is required for the sample amount first added to a reaction system. In this case, measuring other DNA than the target DNA as an internal standard reflecting the sample amount enables to correct the sample amount first added to the reaction system. The internal standard used for correction of the sample amount can be a house keeping gene, ordinarily, of which expression level is believed to show no difference between tissues. For example, the internal standard includes genes of glyceraldehyde phosphate dehydrogenase (GAPDH) being a major enzyme in a glycolysis system, β-actin or γ-actin being a compositional component of a cell skeleton, and S26 being a compositional protein of a ribosome.

An expression level of the Oct-3/4 gene can be determined for the cell exposed to the differentiation inhibiting agent of the present invention. The compound, which has the activity capable of keeping significantly the expression level of Oct-3/4 gene as compared with the expression level of Oct-3/4 gene of a control cell which has not been exposed to the differentiation inhibiting agent of the present invention, that is, which has been differentiated and induced from the embryonic stem cell, is regarded as the differentiation inhibiting agent which maintains undifferentiation of the embryonic stem cell.

Still further another method for screening an optimized culture medium material for keeping undifferentiation of the embryonic stem cell includes a method for detecting such antigen as Stage Specific Embryonic Antigen (hereafter SSEA)-1, SSEA-3, and SSEA-4 which are expressed specifically in undifferentiated cells (Smith et al., Nature 336: p 688, 1988, Solter et al., Proc. Natl. Acad. Sci. U.S.A 75: p 5565, 1978, and Kannagi et al., EMBO J. 2: p 2355, 1983).

In one embodiment, a surface antigen such as SSEA-1 can be labeled by incubating together with a specific antibody (primary antibody) recognizing the antigen and further incubating together with a second antibody (secondary antibody) bound to such reporter as a fluorescence labeling substance. This operation makes the cell expressing the target antigen fluorescent. Subsequently, the labeled cell can be counted and collected separately by employing such a standard method as flow cytometry. Following this step, numbers of labeled and nonlabeled cells can be compared to determine an effect of the target culture medium material. Alternatively, following exposure to a marker antibody of the nonlabeled cell surface, the cell can be exposed to the second antibody specific to an anti-cell surface antigen antibody (for example, anti-SSEA-1 antibody) in ELISA (enzyme-linked immunosorbent assay) manner, and number of cells expressing a desired surface antigen can be quantified by colorimetry or fluorescence measurement. Other methods for quantifying cells expressing surface antigen have been known by those skilled in the art concerning cell culture.

The improved differentiation inhibiting agent, culture method, and culture liquid for proliferation of the stem cells or the embryonic stem cells which are provided according to the present invention, are expected to be applied to all techniques for which the stem cells or the embryonic stem cells are useful.

Cells produced by using the differentiation inhibiting agent, culture method, and culture liquid according to the present invention can be used, after differentiation thereof, for cell transplantation and artificial tissue construction accompanying with the use of an artificial support tissue to use for in vivo transplantation and an artificial organ. Using for cell transplantation therapy and tissue engineering of the stem cell can solve some problems in transplantation therapy, which includes conventional autotransplantation, such as tissue deficit after a transplanting piece is resected from a donor and shortage of the donor. The cell and tissue cultured for transplantation are used for returning to the identical person from whom the cell and tissue were collected, and for transplanting into other person, for medical treatment, and the cell and tissue of the present invention can be used for both purposes.

The differentiation inhibiting agent and/or compound of the present invention or the salt thereof has an excellent stem cell undifferentiation-maintaining and proliferating abilities and, hence, can be used as a remedy for the tissue and the organ damaged by a disease or an injury. Targeted diseases include, for example, burn, intractable skin ulcer, bedsore, hyperplastic scar, birthmark, and tattoo and the like, which are related to a skin; fracture, osteoporosis and the like, which are related to a bone; osteoarthritis, chronic rheumatism, hernia of intervertebral disk, apophysitis, sport damage, which are related to a cartilage; Parkinson's disease, Huntington's disease, Alzheimer's disease, break of a nerve of limb caused by an injury, damage caused by head and neck surgery or thoracic surgery, facial nerve palsy, phrenic nerve damage, intrapelvic nerve damage and the like, which are related to a nerve; alveolar bone damage and anodontia caused by periodontal disease or pyorrhea and the like, which are related to a tooth; male pattern alopecia, which is related to a hair; birth defect, endothelial cell decompensation, opacity caused by cornea infection, cornea degeneration, cornea shape abnormality and the like, which are related to a cornea; hypertension, chronic arterial occlusion, ischemic heart disease and the like, which are related to a blood vessel; myocardial infarction, which is related to a cardiac muscle; diabetes and the like, which are related to a pancreas; hepatitis, hepatic cirrhosis, hepatic failure and the like, which are related to a liver; however, are not restricted to these examples.

VII. Screening for Stat Modulators

The present invention further comprises methods for identifying modulators of Stat1, Stat3 and Stat5. These assays may comprise random screening of large libraries of candidate substances; alternatively, the assays may be used to focus on particular classes of compounds selected with an eye towards structural attributes that are believed to make them more likely to modulate the function of the Stat molecule.

To identify a Stat1, Stat3 or Stat5 modulator, one generally will determine the functional activity of the Stat molecule in the presence and absence of the candidate compound, a modulator defined as any substance that alters function. For example, a method generally comprises: providing a candidate modulator; contacting the candidate modulator with a screening cell; measuring one or more characteristics of the cell; and comparing the characteristic of the cell with the characteristic of the cell in the absence of said candidate modulator, wherein a difference between the measured characteristics indicates that said candidate modulator is, indeed, a modulator of the cell. In a further embodiment, the invention is directed to a method for screening for a Stat1, Stat3 or Stat5 activator. The method includes incubating a cell, having a Stat regulatory element operatively linked to a reporter construct (e.g., Stat-3 cell lines deposited under ATCC Nos., deposited on, Stat-1 cell lines deposited under ATCC Nos. [ ], deposited on and Stat-5 cell lines deposited under ATCC Nos. [ ], deposited on), in the presence and absence of a candidate modulator, and detecting a signal (e.g., luciferase signal) from the reporter construct. An increase in the signal in the presence of the candidate modulator when compared with the signal in the absence of said candidate modulator is indicative of a Stat activator.

In yet another aspect, the invention is directed to a method for screening for a Stat1, Stat3 or Stat5 inhibitor. The method involves incubating a cell, having a Stat regulatory element operatively linked to a reporter construct, in the presence and absence of a candidate modulator and detecting a signal from the reporter construct (e.g., Stat-3 cell lines deposited under ATCC Nos., deposited on, Stat-1 cell lines deposited under ATCC Nos. [ ], deposited on and Stat-5 cell lines deposited under ATCC Nos. [ ], deposited on). A decrease in the signal in the presence of the candidate modulator when compared with the signal in the absence of the candidate modulator is indicative of a Stat inhibitor. Further, illustrations of the screening methods of the current invention are described in the Examples.

VIII. Kits

The present invention also encompasses a finished packaged and labeled pharmaceutical product or Stat modulator screening products. This article of manufacture includes the appropriate unit dosage form in an appropriate vessel or container such as a glass vial or other container that is hermetically sealed. The pharmaceutical product may contain, for example, a compound of the invention in a unit dosage form in a first container, and in a second container, sterile water for injection. Alternatively, the unit dosage form may be a solid suitable for oral, transdermal, intranasal, or topical delivery.

In a specific embodiment, the unit dosage form is suitable for intravenous, intramuscular, intranasal, oral, topical or subcutaneous delivery. Thus, the invention encompasses solutions, preferably sterile, suitable for each delivery route.

As with any pharmaceutical product, the packaging material and container are designed to protect the stability of the product during storage and shipment. Further, the products of the invention include instructions for use or other informational material that advise the physician, technician or patient on how to appropriately prevent or treat the disease or disorder in question. In other words, the article of manufacture includes instruction means indicating or suggesting a dosing regimen including, but not limited to, actual doses, monitoring procedures, cancer cell counts, and other monitoring information.

Specifically, the invention provides an article of manufacture comprising packaging material, such as a box, bottle, tube, vial, container, sprayer, insufflator, intravenous (i.v.) bag, envelope and the like; and at least one unit dosage form of a pharmaceutical agent contained within said packaging material, wherein said pharmaceutical agent comprises a compound of the invention, and wherein said packaging material includes instruction means which indicate that said compound can be used to prevent, manage, treat, and/or ameliorate one or more symptoms associated with cancer, or one or more symptoms thereof by administering specific doses and using specific dosing regimens as described herein.

EXAMPLES

Example 1

Development of Reporter Cell Systems

A cell-based assay system for each Stat1, Stat3 and Stat5 was developed to identify compounds that modulate the respective Stat activity. Although the details for each system are slightly different, as described below, the basic principle are the same. Appropriate cell lines (NIH3T3 for Stat1, U3A for Stat3, and T47D for Stat5) were transfected with a plasmid containing a luciferase reporter gene under the control of a promoter responsive to the indicated Stat, e.g., Stat1, Stat3 or Stat5, as well as a neomycin phosphotransferase cassette (BRIGHT GLO Luciferase Assay Kit available from Promega (Madison, Wis.). The reporter plasmid used in the Stat1 and Stat3 cell lines is described in Lynch et al., Cancer Research, 67:1254-61 (2007), which is herein incorporated by reference in its entirety. The nuclic acid binding sequence of Stat5 use in the reporter plasmid is denoted as region B in Walker et al., Oncogene, 26:224-233 (2007), which is herein incorporated by reference in its entirety.

Cells were selected in geneticin (G418) to isolate clones that had stably integrated the plasmid. Individual clones were isolated and luciferase expression was measured by luminometry in the presence and absence of a stimulator of the specific Stat of interest. Clones having a low basal luciferase expression, prominent induction by a specific stimulus (IFN-γ for Stat1, (IL)-6 for Stat3 and prolactin for Stat5), no induction with an irrelevant stimulus, and stable properties after prolonged cell culture or cryopreservation and thawing were selected. Multiple such clones for each reporter system were isolated. Several of these cell lines for each Stat construct were deposited with American Type Culture Collection of Manassas, Va. For example, cell lines having the Stat1 inducible promoter were deposited under ATCC Nos. Cell lines having the Stat3 inducible promoter were deposited under ATCC Nos. Cell lines having the Stat5 inducible promoter were deposited under ATCC numbers Nos.

A parallel system was also developed in which luciferase was under the control of the transcription factor NF-κB (cell lines deposited on under ATCC Nos.). When these 293T cells are treated with tumor necrosis factor (TNF)-α, they show prominent induction of luciferase. This provided an independent control to exclude non-specific effects.

To ensure the specificity of the reporter systems, the Stat3 reporter cell line and the NF-κB reporter system were compared. Each cell type was either untreated, treated with IL-6 (which activates Stat3 in both systems) or treated with TNF-α (which activates NF-κB in both). IL-6 led to approximately a five-fold induction of luciferase in the Stat3 reporter system, but induced no change in the NF-κB reporter cells. Conversely, TNF-α induced a 12-fold induction of luciferase in the NF-κB reporter cells, but led to no change in the Stat3-reporter system. The Stat1 and Stat5 reporter systems show similar characteristics. All three cell-based screens are able to reproducibly identify active and specific compounds.

Example 2

Identifying Stat Modulators

All three cell-based screening systems were adapted for use in 384-well plates, which were then used to screen a library of 1120 compounds (the Prestwick Myeloma Collection available from Prestwick Chemical, Illkirch, France). The library constituents are FDA-approved drugs or compounds that have otherwise been used safely in humans. Briefly, 2,500 cells are plated per well in 30 μl of medium in a 384 well plate and grown in Dulbecco's modified Eagle's medium (DMEM) supplemented with 10% fetal calf serum in an incubator with a 95% air/5% $CO_2$ atmosphere at 37° C. After a 16 hour incubation to allow cells to adhere, 100 nl of the test compound is added per well and incubated for one hour, after which the activating cytokine (IFN-γ, IL-6, and prolactin, respectively) are added to each well in 10 μl of medium. After 6 hours, 40 μl of 0.5× Bright-Glo luciferase substrate (diluted in PBS) is added, and luciferase activity is quantitated on a Luminoskan luminometer (Helsinki, Finland).

The compounds that show selective activity in the primary screen (e.g., 25% or more difference in luciferase activity in the presence versus the absence of the compound and less than 12% difference in luciferase activity in the Nf-κB assay in the presence versus the absence of the compound) were then validated in a dose-response assay using the appropriate reporter cell lines.

This is followed by another confirmation assay utilizing quantitative real-time PCR measuring expression of endogenous target genes of each Stat. In this assay the cells are incubated as described above. However, after the incubation the cells are lysed and assessed for increased or decreased expression of target genes specific for the respective Stat molecule, e.g., Stat1, interferon-responsive factor (IRF)-1, GADD45☐, and IFI-16; for Stat3, SOCS3, BCL-6, and KLF-4; and, for Stat5, CIS, PIM-1, and MMP3.

As a tertiary screen, biological assays which are indicative of Stat1, Stat3 or Stat5 modulation were tested with the compounds identified in the screens. For Stat1, the growth inhibition of 2fTGH fibrosarcoma cells treated with IFN-γ (Pellegrini S, et al. Mol Cell Biol 1989; 9:4605-4612) is measured. For Stat3, the survival of U266 myeloma cells (Catlett-Falcone Ret al. Immunity 1999; 10:105-115) is assayed and for Stat5, the survival of Ba/F3 pro-lymphocytic leukemia cells transformed with Bcr/Abl (Carlesso N, etr al. J. Exp. Med 1996; 183:811-820) is assayed.

Figure 5A:
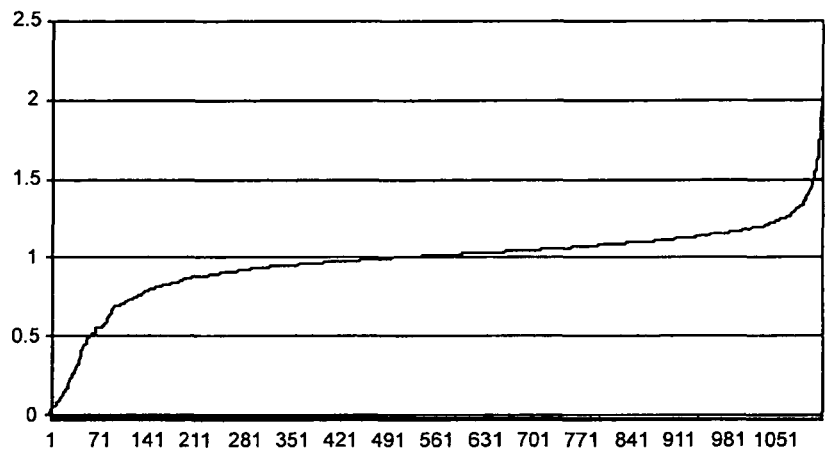
FIG. 5 illustrates the effect of the 1120 compounds of the library on Stat3 (FIG. 5A) and NF-κB (FIG. 5B) activity.
Figure 5B:
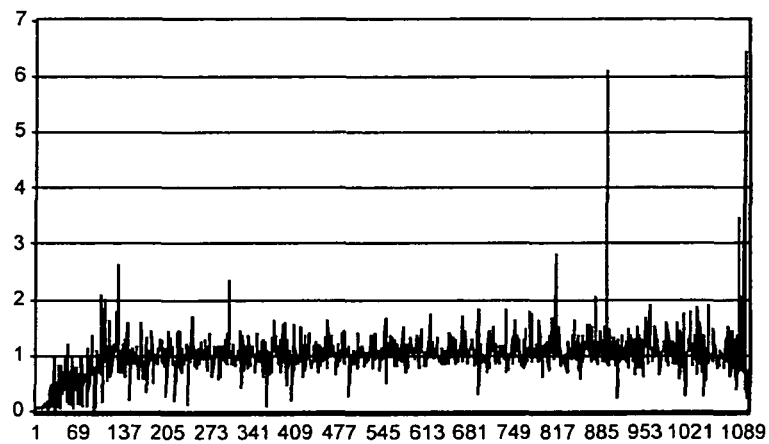

Most of the compounds tested had no effect on Stat3-dependent luciferase activity. (FIG. 5) This reflects the fact that this cellular system is extremely stable, and these diverse drugs would be unlikely to alter this specific target. However, a small fraction of the compounds led to a prominent inhibition of Stat3-dependent luciferase activity. FIG. 5A depicts relative luciferase activity (1 of y-axis defined as luciferase activity in the absence of any test compound) of each of the 1120 drugs of the Prestwick Myeloma Collection from lowest Stat3 dependent luciferase activity to highest Stat3 dependent luciferase activity. Many of these compounds also inhibited NF-κB activity (FIG. 5B; e.g., see compounds at far left of x-axis) and were thus non-specific and excluded from further analysis. However, the compounds that inhibited both included cytotoxic agents (doxorubicin, mitoxantrone, daunorubicin), protein synthesis inhibitors (cycloheximide) or DNA intercalating agents (propidium iodide).

Figure 6:
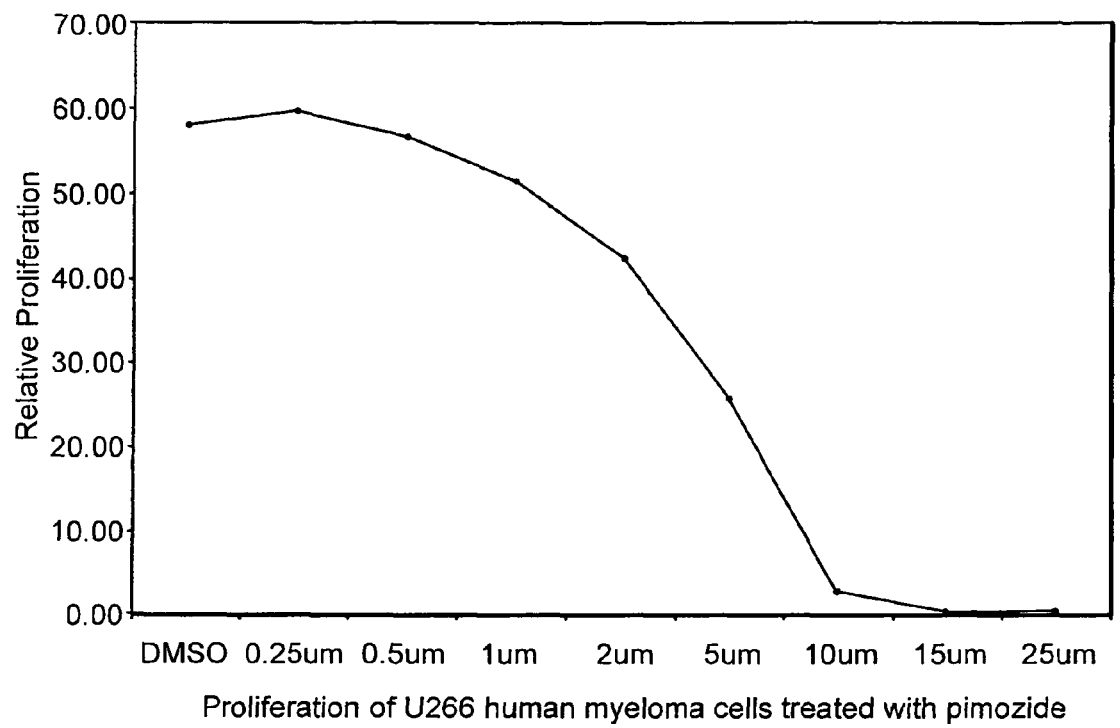
FIG. 6 illustrates that proliferation of U266 cells is inhibited when contacted with pimozide.

The small number of compounds that selectively inhibited Stat3 (or NF-κB) were further pursued. These compounds were tested individually, and dose responses were analyzed. Each of these compounds was found to significantly and specifically inhibit Stat3 activity in these validation studies. The drugs identified in this screen included pyrimethamine, pimozide, guanabenz acetate, alprenolol hydrochloride, nifuroxazide, solanine alpha, fluoxetine hydrochloride, ifosfamide, pyrvinium pamoate and moricizine hydrochloride, 3-(1,3-benzodioxol-5-yl)-1,6-dimethyl-pyrimido[5,4-e]-1,2,4-triazine-5,7(1H,6H)-dione or 3-(2-hydroxyphenyl)-3-phenyl-N,N-dipropylpropanamide. One such compound is pimozide, a drug used to decrease tics in patients with Tourette's disorder. When U266 cells were treated with pimozide, they showed a dose-dependent decrease in survival (FIG. 6).

It was also observed that a small number of compounds specifically enhance Stat3 function (FIG. 5). These drugs included mebendazole, nocodazole, nortriptyline hydrochloride, zimelidine dihydrochloride monohydrate, adenosine 5'-monophosphate monohydrate, promazine hydrochloride, podophyllotoxin, ribavirin, deptropine citrate, or 4-(3,4-Dimethyl-phenoxy)-N-hydroxy-benzamidine.

Figure 7:
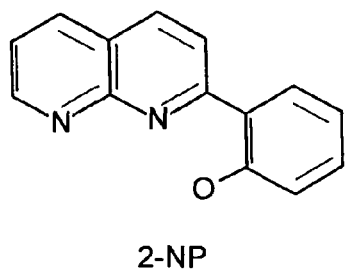
FIG. 7 illustrates the chemical structure of the Stat1 activator 2-(1,8-Naphthyridin-2-yl)phenol.
Figure 8:
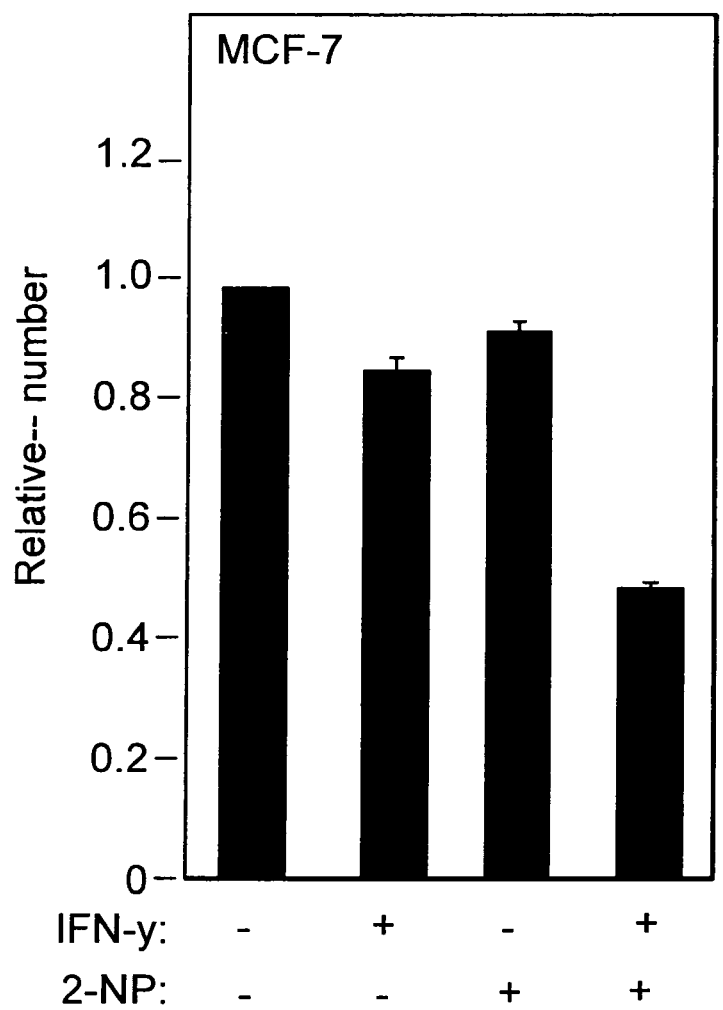
FIG. 8 shows that 2-(1,8-Naphthyridin-2-yl)phenol enhances the Stat1 dependent growth inhibitory effects of IFN-γ in MCF-7 breast cancer cells.

An independent screen for enhancers of Stat1 function was also performed. Using a 384-well format, several independent libraries from Prestwick and Chembridge were screened. Several active and specific Stat1 activators were identified including One of these compounds, 2-(1,8-Naphthyridin-2-yl)phenol (2-NP) (FIG. 7), enhanced the expression of endogenous Stat1 genes, and accentuated the growth inhibitory effects of IFN-γ on human breast cancer cell lines in a Stat1-dependent manner (FIG. 8). Mechanistic studies indicated that 2-NP functions by increasing the magnitude and duration of Stat1 tyrosine phosphorylation.

All patents, patent applications, and published references cited herein are hereby incorporated by reference in their entirety. While this invention has been particularly shown and described with references to preferred embodiments thereof, it will be understood by those skilled in the art that various changes in form and details may be made therein without departing from the scope of the invention encompassed by the appended claims.

What is claimed is:

1. A method for inhibiting Stat3 activity in a cell, comprising contacting said cell with an effective dose of a compound selected from the group consisting of pyrimethamine, pimozide, guanabenz acetate, alprenolol hydrochloride, nifuroxazide, solanine alpha, fluoxetine hydrochloride, ifosfamide, pyrvinium pamoate, moricizine hydrochloride, 3-(1,3-benzodioxol-5-yl)-1,6-dimethyl-pyrimido[5,4-e]-1,2,4-triazine-5,7(1H,6H)- dione and 3-(2-hydroxyphenyl)-3-phenyl-N,N-dipropylpropanamide or a salt or ester thereof and detecting Stat3 activity in said cell.

2. The method of claim 1, wherein said Stat3 activity is selected from the group consisting of Stat3 phosphorylation, Stat3 dimmerization, Stat3 binding to a polynucleotide comprising a Stat3 binding site, activation of a Stat3 responsive gene and Stat3 nuclear translocation.

3. The method of claim 2, wherein said Stat3 responsive gene is selected from the group consisting of Egr-1, JunB, cyclin D1, Mcl-1, Bcl-2, Bcl-xl and survivin.

4. The method of claim 1, wherein said cell is transfected with a nucleic acid encoding Stat3.

5. A method for inducing Stat3 activity in a cell, comprising contacting said cell with an effective dose of a compound selected from the group consisting of mebendazole, nocodazole, nortriptyline hydrochloride, zimelidine dihydrochloride monohydrate, adenosine 5'-monophosphate monohydrate, promazine hydrochloride, podophyllotoxin, ribavirin, deptropine citrate, and 4-(3,4Dimethyl-phenoxy)-N-hydroxy-benzamidine or a salt or ester thereof and detecting Stat3 activity in said cell.

6. The method of claim 5, wherein said Stat3 activity is selected from the group consisting of Stat3 phosphorylation, Stat3 dimmerization, Stat3 binding to a polynucleotide comprising a Stat3 binding site, activation of a Stat3 responsive gene and Stat3 nuclear translocation.

7. The method of claim 6, wherein said Stat3 responsive gene is selected from the group consisting of Egr-1, JunB, cyclin D1, Mcl-1, Bcl-2, Bcl-xl and survivin.

8. The method of claim 5, wherein said cell is transfected with a nucleic acid encoding Stat3.

* * * * *